(12) United States Patent
Hashimshony

(10) Patent No.: US 8,195,282 B2
(45) Date of Patent: Jun. 5, 2012

(54) METHOD AND APPARATUS FOR EXAMINING TISSUE FOR PREDEFINED TARGET CELLS, PARTICULARLY CANCEROUS CELLS, AND A PROBE USEFUL IN SUCH METHOD AND APPARATUS

(75) Inventor: Dan Hashimshony, Givat Ada (IL)

(73) Assignee: Dune Medical Devices Ltd, South Caesarea ( * ) Notice: Subject to any disclaimer, the term of this patent is extended or adjusted under 35 U.S.C. 154(b) by 11 days.

(21) Appl. No.: 11/743,027

(22) Filed: May 1, 2007

(65) Prior Publication Data

US 2007/0260156 A1  Nov. 8, 2007

Related U.S. Application Data

(63) Continuation of application No. 10/298,196, filed on Nov. 18, 2002, now Pat. No. 7,505,811.

(60) Provisional application No. 60/331,548, filed on Nov. 19, 2001, provisional application No. 60/343,583, filed on Jan. 2, 2002.

(51) Int. Cl.
| | |
|---|---|
| A61B 5/04 | (2006.01) |
| A61B 5/05 | (2006.01) |
| A61B 10/00 | (2006.01) |
| A61B 5/103 | (2006.01) |
| A61B 5/117 | (2006.01) |
| A61B 17/00 | (2006.01) |
| A61B 18/18 | (2006.01) |

(52) U.S. Cl. ........ 600/547; 600/372; 600/382; 600/562; 600/587; 324/600; 324/642; 606/1; 606/13; 607/901

(58) Field of Classification Search .................. 600/547, 600/431, 372, 382, 562, 587; 324/600; 606/1, 606/13; 607/901
See application file for complete search history.

(56) References Cited

U.S. PATENT DOCUMENTS 3,830,224 A  8/1974  Vanzetti et al.
(Continued)

FOREIGN PATENT DOCUMENTS

DE  3637549 A1  5/1988
(Continued)

OTHER PUBLICATIONS

V. Rajshekhar, "Continuous impedance monitoring during CT-guided stereotactic surgery: relative value in cycstic and solid lesions", British Journal of Neurosurgery, vol. 6, 1992, pp. 439-444.

(Continued)

*Primary Examiner* — Sean Dougherty
(74) *Attorney, Agent, or Firm* — Browdy and Neimark, PLLC

(57) ABSTRACT

A method, apparatus and probe for examining tissue for the presence of target cells, particularly cancerous cells, by subjecting the tissue to be examined to a contrast agent containing small particles of a physical element conjugated with a biological carrier selectively bindable to the target cells. Energy pulses are applied to the examined tissue. The changes in impedance and/or optical characteristics of the examined tissue produced by the applied energy pulses are detected and utilized for determining the presence of the target cells in the examined tissue. In a described preferred embodiment, the applied energy pulses include laser pulses, and the physical element conjugated with a biological carrier is a light-sensitive semiconductor having an impedance which substantially decreases in the presence of light. The same probe used for detecting the targeted cells may also be used for destroying the cells so targeted.

39 Claims, 11 Drawing Sheets

U.S. PATENT DOCUMENTS

| | | | |
|---|---|---|---|
| 4,291,708 A | 9/1981 | Frei et al. | |
| 4,344,440 A | 8/1982 | Aaby et al. | |
| 4,458,694 A | 7/1984 | Sollish et al. | |
| 4,537,203 A | 8/1985 | Machida | |
| 4,539,640 A | 9/1985 | Fry et al. | |
| RE32,000 E | 10/1985 | Sagi | |
| 4,617,939 A | 10/1986 | Brown et al. | |
| 4,625,171 A | 11/1986 | Sekihara et al. | |
| 4,682,594 A | 7/1987 | Mok | |
| 4,689,567 A | 8/1987 | Maudsley | |
| 4,751,464 A | 6/1988 | Bridges | |
| 4,768,513 A | 9/1988 | Suzuki | |
| 4,785,806 A | 11/1988 | Deckelbaum | |
| 5,115,137 A | 5/1992 | Andersson-Engels et al. | |
| 5,143,079 A | 9/1992 | Frei et al. | |
| 5,227,730 A | 7/1993 | King et al. | |
| 5,442,290 A | 8/1995 | Crooks | |
| 5,482,041 A | 1/1996 | Wilk et al. | |
| 5,558,092 A | 9/1996 | Unger et al. | |
| 5,572,132 A | 11/1996 | Pulyer et al. | |
| 5,630,426 A | 5/1997 | Eggers et al. | |
| 5,704,355 A | 1/1998 | Bridges | |
| 5,727,569 A | 3/1998 | Benetti et al. | |
| 5,735,278 A | 4/1998 | Hoult et al. | |
| 5,744,971 A | 4/1998 | Chan et al. | |
| 5,758,646 A | 6/1998 | Van Der Meulen et al. | |
| 5,800,350 A | 9/1998 | Coppleson et al. | |
| 5,807,257 A | 9/1998 | Bridges | |
| 5,807,272 A * | 9/1998 | Kun et al. | 600/547 |
| 5,810,742 A | 9/1998 | Pearlman | |
| 5,821,410 A | 10/1998 | Xiang et al. | |
| 5,829,437 A | 11/1998 | Bridges | |
| 5,884,239 A | 3/1999 | Romanik, Jr. | |
| 5,900,618 A | 5/1999 | Anlage et al. | |
| 5,927,284 A | 7/1999 | Borst et al. | |
| 6,010,455 A | 1/2000 | Barnett et al. | |
| 6,026,323 A | 2/2000 | Skladnev et al. | |
| 6,055,452 A | 4/2000 | Pearlman | |
| 6,061,589 A | 5/2000 | Bridges et al. | |
| 6,090,041 A | 7/2000 | Clark et al. | |
| 6,109,270 A | 8/2000 | Mah et al. | |
| 6,135,968 A | 10/2000 | Brounstein et al. | |
| 6,167,297 A | 12/2000 | Benaron | |
| 6,173,604 B1 | 1/2001 | Xiang et al. | |
| 6,233,479 B1 | 5/2001 | Haddad et al. | |
| 6,258,576 B1 | 7/2001 | Richards-Kortum et al. | |
| 6,280,704 B1 | 8/2001 | Schutt et al. | |
| 6,287,302 B1 | 9/2001 | Berube | |
| 6,308,097 B1 | 10/2001 | Pearlman | |
| 6,315,981 B1 | 11/2001 | Unger | |
| 6,321,106 B1 | 11/2001 | Lemelson | |
| 6,331,166 B1 | 12/2001 | Burbank et al. | |
| 6,370,426 B1 | 4/2002 | Campbell et al. | |
| 6,375,634 B1 | 4/2002 | Carroll | |
| 6,377,841 B1 | 4/2002 | Lin et al. | |
| 6,397,095 B1 | 5/2002 | Eyuboglu et al. | |
| 6,405,733 B1 | 6/2002 | Fogarty et al. | |
| 6,432,064 B1 * | 8/2002 | Hibner et al. | 600/564 |
| 6,500,112 B1 | 12/2002 | Khouri | |
| 6,530,944 B2 | 3/2003 | West et al. | |
| 6,546,787 B1 | 4/2003 | Schiller et al. | |
| 6,564,806 B1 | 5/2003 | Fogarty et al. | |
| 6,597,185 B1 | 7/2003 | Talanov et al. | |
| 6,671,540 B1 | 12/2003 | Hochman | |
| 6,677,755 B2 | 1/2004 | Belt et al. | |
| 6,695,782 B2 | 2/2004 | Ranucci et al. | |
| 6,699,206 B2 | 3/2004 | Burbank et al. | |
| 6,722,371 B1 | 4/2004 | Fogarty et al. | |
| 6,728,565 B2 | 4/2004 | Wendlandt | |
| 6,741,077 B2 | 5/2004 | Yokoyama et al. | |
| 6,747,454 B2 | 6/2004 | Belt | |
| 6,752,154 B2 | 6/2004 | Fogarty et al. | |
| 6,766,185 B2 | 7/2004 | Scott | |
| 6,788,966 B2 * | 9/2004 | Kenan et al. | 600/372 |
| 6,813,515 B2 | 11/2004 | Hashimshony | |
| 6,840,948 B2 | 1/2005 | Albrecht et al. | |
| 6,909,084 B2 | 6/2005 | Tachi et al. | |
| 6,962,587 B2 | 11/2005 | Johnson et al. | |
| 7,015,701 B2 * | 3/2006 | Wiegand et al. | 324/603 |
| 7,082,325 B2 | 7/2006 | Hashimshony et al. | |
| 7,184,824 B2 | 2/2007 | Hashimshony | |
| 2001/0051774 A1 | 12/2001 | Littrup et al. | |
| 2002/0055754 A1 | 5/2002 | Ranucci et al. | |
| 2002/0059938 A1 | 5/2002 | Fogarty et al. | |
| 2002/0068880 A1 | 6/2002 | Burbank et al. | |
| 2002/0120265 A1 | 8/2002 | Fowler | |
| 2003/0045798 A1 | 3/2003 | Hular et al. | |
| 2003/0062897 A1 | 4/2003 | Belt et al. | |
| 2003/0117140 A1 | 6/2003 | Belt et al. | |
| 2003/0138378 A1 | 7/2003 | Hashimshony | |
| 2003/0171664 A1 | 9/2003 | Wendlandt | |
| 2003/0187366 A1 | 10/2003 | Hashimshony | |
| 2003/0199753 A1 | 10/2003 | Hibner et al. | |
| 2003/0229343 A1 | 12/2003 | Albrecht et al. | |
| 2004/0168692 A1 | 9/2004 | Fogarty et al. | |
| 2005/0010131 A1 | 1/2005 | Burbank et al. | |
| 2005/0021019 A1 | 1/2005 | Hashimshony | |
| 2005/0107717 A1 | 5/2005 | Yamamoto et al. | |
| 2006/0264738 A1 | 11/2006 | Hashimshony et al. | |

FOREIGN PATENT DOCUMENTS

| | | |
|---|---|---|
| WO | 97/12553 A1 | 4/1997 |
| WO | 01/43630 A2 | 6/2001 |
| WO | 0165240 A1 | 9/2001 |
| WO | 03060462 A2 | 7/2003 |
| WO | 2005009200 A2 | 2/2005 |
| WO | 2005089065 A2 | 9/2005 |
| WO | 2006072947 A2 | 7/2006 |
| WO | 2006092797 A2 | 9/2006 |
| WO | 2006103665 A2 | 10/2006 |
| WO | 2007015255 A2 | 2/2007 |

OTHER PUBLICATIONS

Section on Biomedical Stochastic Physics (SBSP), "Subsurface Spectroscopy", http://www.sbsp-limb.nichd.nih.gov/html/spectroscopy.html. Apr. 1, 2005.

K. Harzbecker et al., "Thermographic thorax diagnostics", Z. Gesamte Inn. Med., Feb. 1978, 1;33(3):78-80 Abstract only (article in German).

Dexter LI Kondrat'ev VB.,"Thermography in different diagnoisi of lymphostasis in the lower limbs", Vestin Khir Im I. I Grek. Jun. 1976;116(6):60-4 Abstract only (article in Russian).

Ascension Products Ltd., MiniBIRD 500 & 800, downloaded on Mar. 15, 2005, http://www.ascension-tech.com/products/minibird.php.

D. Misra et al., "Noninvasive Electrical Characterization of Materials at Microwave Frequencies Using an Open-Ended Coaxial Line: Test of an Improved Calibration Technique", IEEE Transactions on Microwave Theory & Techniques, 38:(1):8-13, 1990.

E. Burdette et al., "In Vivo Probe Measurement Technique for Determining Dielectric Properties at VHF Through Microwave Frequencies", IEEE Transactions on Microwave Theory & Techniques, MTT-28(4):414-427, 1980.

Y. Xu et al., "Measurement of Microwave Permittivity Using Open Ended Elliptical Coaxial Probes", IEEE Transactions on Microwave Theory & Techniques, 40(1): 143-150, 1992.

M. Stuchly et al., "Measurement of Radio Frequency Permittivity of Biological Tissues with an Open-Ended Coaxial Line: Part II—Experimental Results", IEEE Transactions on Microwave Theory & Techniques, MTT-30(1): 87-91, 1982.

J. Mosig et al., "Reflection of an Open-Ended Coaxial Line and Application to Nondestructive Measurement Materials", IEEE Transactions on Instrumentation and Measurement, IM-30(1):46-51, 1981.

D. Smith et al., "In Vivo Measurement of Tumor Conductiveness with the Magnetic Bioimpedance Method", IEEE Transactions on Biomedical Engineering, vol. 47, No. 10, Oct. 2000.

L. G. Brown, "A Survey of Image Registration Techniques", ACM Computing Surveys, 24(4):325-376, 1992.

M. Beard et al., "Size-Dependent Photoconductivity in CdSe Nanoparticles as Measured by Time-Resolved Terahertz Spectroscopy", Nano Letters, 2(9), 983-987, Aug. 14, 2002, Abstract only.

M. Akerman et al., "Nanocrystal targeting in vivo", PNAS, 99(20), 12617-12621, Oct. 1, 2002.

A. J. Surowiec et al., "Dielectric Properties of Breast Carcinoma and the Surrounding Tissues", IEEE Transactions on Biomedical Engineering, vol. 35, No. 4, Apr. 1988.

H. P. Schwan, "Mechanisms responsible for electrical properties of tissues and cell suspensions", Medical Progress Through Technology, 19:163-165, 1993.

J. G. Proakis et al., "Digital Signal Processing: Principles, Algorithms, and Applications", Third Edition, Prentice Hall International Inc., Chapter 4, Table of Contents and cover page only.

"Affinity Biosensors: Techniques and Protocols", Edited by K. R. Rogers and A. Mulchandani, Humana Press, New Jersey, USA, 1998, Table of Contents pages only.

Journal: Biosensors & Bioelectronics, vol. 20, Issue 8, pp. 1459-1695, Feb. 15, 2005, Table of Contents pages only.

Journal: Biosensors & Bioelectronics, vol. 20, Issue 6, pp. 1029-1295, Dec. 15, 2004, Table of Contents pages only.

Journal: Biosensors & Bioelectronics, vol. 20, Issue 5, pp. 917-1028, Nov. 15, 2004, Table of Contents pages only.

Journal: Biosensors & Bioelectronics, vol. 20, Issue 1, pp. 1-142, Jul. 30, 2004, Table of Contents pages only.

Journal: Biosensors & Bioelectronics, vol. 20, Issue 12, pp. 2387-2593, Jun. 15, 2005, Table of Contents pages only.

Journal: Sensors & Actuators B (Chemical), vol. 103, Issues 1-2, pp. 1-473, Sep. 29, 2004, Table of Contents pages only.

Journal: Sensors & Actuators B (Chemical), vol. 102, Issue 1, pp. 1-177, Sep. 2004, Table of Contents pages only.

Journal: Sensors & Actuators B (Chemical), vol. 106, Issue 1, pp. 1-488, Apr. 29, 2005, Table of Contents pages only.

Sensors: A Comprehensive Survey—vol. 2: Chemical and Biochemical Sensors, Part I, Edited by W. Goepel, J. Hesse, J. N. Zemel, (VCH, 1991), Table of Contents pages only.

Sensors: A Comprehensive Survey—vol. 3: Chemical and Biochemical Sensors, Part 2, Edited by W. Goepel, J. Hesse, J. N. Zemel, (VCH, 1992), Table of Contents pages only.

Sensors: A Comprehensive Survey—vol. 7: Mechanical Sensors, Part 2, Edited by W. Goepel, J. Hesse, J. N. Zemel, (VCH, 1994), Table of Contents pages only.

Y. Kinouchi et al., "Fast in vivo Measurement of Local Tissue Impedances Using Needle Electrodes", Med. Biol. Eng. Comput. 35(9). 486-492, 1997—Abstract only.

R. Pethig, "Dielectric and Electronic Properties of Biological Materials", John Wiley & Sons, 1979, Cover and Table of Contents pages only.

S. Grimnes et al., "Bioimpedance and Bioelectricity Basics" Academic Press, Cover and Table of Contents pages only.

K. S. Cole, "Membranes, Ions and Impulses": A Chapter of Classical Biophysics, 1968, Cover and Table of Contents pages only.

J. G. Proakis et al., "Digital Signal Principles, Algorithms, and Applications", Third Edition, Prentice Hall International Inc., Chapter 4, Table of Contents and cover page only. 1996.

S. Grimnes et al., "Bioimpedance and Bioelectricity Basics" Academic Cover and Table of Contents pages only. 2000.

* cited by examiner

Cells containing the specific proteins

After injection to the blood stream, the antibodies attached to the cells proteins Impedance measurement electrodes Impedance measurement electrodes Light beam After injection with the light beam, the surface is changed due to the change in conductivity of the Silicon balls From spectrometer I From spectrometer II At $w_0$, the relation between Polarization is a/b
in general   $a = a(w)$
             $b = b(w)$ $c = \frac{a}{b} = c(w)$ is the polarization function

METHOD AND APPARATUS FOR EXAMINING TISSUE FOR PREDEFINED TARGET CELLS, PARTICULARLY CANCEROUS CELLS, AND A PROBE USEFUL IN SUCH METHOD AND APPARATUS

RELATED APPLICATIONS

The present application is related to, and claims the priority dates of, U.S. Provisional Application 60/331,548 filed Nov. 19, 2001, and U.S. Provisional Application 60/343,583 filed Jan. 2, 2002: the contents of both applications are incorporated herein by reference. The present application is also related to my prior U.S. application Ser. No. 10/035,428, filed Jan. 4, 2002, the contents of which are also incorporated herein by reference.

FIELD AND BACKGROUND OF THE INVENTION

The present application relates to a method and apparatus for examining tissue for the presence of predefined target cells therein, and also to a probe for use in such method and apparatus. The invention is particularly useful for detecting cancerous cells in a real-time manner during a surgical operation for removing, e.g., a breast tumor. The invention is therefore described below with respect to such an application, but it will be appreciated that the invention is useful in many other applications.

During a surgical operation for the removal of a tumor, it would be highly desirable to provide the surgeon with a real-time indication of the nature of the tissue at the surgical site, i.e., whether it is normal tissue or cancerous tissue. In the absence of such a real-time indication, the surgeon may remove more tissue than really necessary in order to provide better assurance that the entire tumor is removed.

Existing medical instruments, such as computed tomography (CT) scanners, magnetic resonance imagining (MRI) devices, electrical bioimpedance scanning devices (T-scan), ultrasound and other similar instruments, are commonly used in pre-operative guided biopsy procedures to obtain samples of tissues in order to delineate the extent of the cancerous tissue. However, the accuracy of such instruments and procedures for the delineation of cancerous tissue depends to a high degree on the accuracy by which the sample was taken, and the expertise of the surgeon in translating such information to the actual conditions at the tumor site.

My above-cited U.S. patent application Ser. No. 10/035, 428, the contents of which are incorporated herein by reference, briefly reviews various electrical techniques described in the prior art for examining tissue in order to indicate its nature according to the dielectric properties of the examined tissue. That patent application is directed to an improved method of making such an examination, by applying an electrical pulse (or a sequence of pulses) to the tissue to be examined via a probe, which generates an electrical field in the examined tissue and produces a reflected pulse therefrom. The reflected electrical pulse is detected, and its electrical characteristics are compared with those of the applied electrical pulse to provide an indication of the dielectric properties of the examined tissue, and thereby, the extent of the presence of cancerous cells therein.

However, because of the critical importance of this information to the surgeon during a surgical operation, efforts are continually being made to provide methods, apparatus and probes, which are capable of more accurately determining the extent of the presence of cancerous cells in a real-time manner.

OBJECTS AND BRIEF SUMMARY OF THE PRESENT INVENTION

An object of the present invention is to provide a method for examining tissue which is basically an electrical optical measuring technique, but which is capable of more accurately determining the extent of the presence of cancerous cells, as well as other predefined target cells, in an examined tissue. Another object of the invention is to provide a method for destroying the target cells immediately after detection. Another object of the invention is to provide apparatus for use in the novel method, and a further object is to provide a probe particularly useful in such apparatus.

According to one aspect of the present invention, there is provided a method of examining tissue for the presence of predefined target cells therein, comprising: subjecting the tissue to be examined to a contrast agent containing small particles of a physical element conjugated with a biological carrier, e.g., an antibody, selectively bindable to the target cells; applying energy pulses to the examined tissue; detecting changes in electrical properties of the examined tissue produced by the applied energy pulses; and utilizing the detected changes in electrical properties for determining the presence of the target cells in the examined tissue.

As indicated earlier, the method is particularly useful for detecting cancer target cells in a real-time manner during a surgical operation, and therefore the invention is described below particularly with respect to this application.

As will be described more particularly below, the novel method exploits the known technique for localization of tumors by the injection of physical elements conjugated with a biological carrier such as an antibody selectively bindable to the cancerous cells. Such techniques have been used with radioisotopes in order to target tumor tissue or cancerous cells when examined with computer tomography. Techniques using nano/micro crystal particles have also been used as novel intravascular probes for both diagnostic (e.g., imaging) purposes and therapeutic (e.g., drug delivery) purposes. For example, reference is made to the publications Akerman, M. E., et al., Nanocrystal Targetting in vivo, PNAS, Oct. 1, 2002, 12617-12621; and Beard, M. C., et al., Size-Dependent Photoconductivity in CdSe Nanoparticles as Measured by Time-Resolved Terahertz Spectroscopy, American Chemical Society, Aug. 14, 2002, the contents of which publications are incorporated herein by reference.

The present invention utilizes such a technique (e.g., with non-radioactive conjugated antibodies) in an electric optical measuring procedure for detecting cancerous cells. Preferably, the applied energy pulses include pulses of optical (e.g., laser) energy, and the physical element conjugated with the antibody is one which changes in impedance when illuminated by the optical energy. As described more particularly below, especially good results are obtainable when the physical element is a light-sensitive semiconductor having an impedance which substantially decreases in the presence of light. In the preferred embodiments described below, changes in optical properties of the examined tissue produced by the applied optical pulses are also detected and utilized in determining the extent of the presence of the target (e.g., cancer) cells in the examined tissue.

While particularly good results are obtainable when the physical element conjugated with the antibody is a light-sensitive semiconductor, the invention may also be implemented in applications wherein the physical element is a metal having good light reflecting characteristics, and wherein changes in an optical characteristic (e.g., frequency, amplitude and/or phase) of the reflected light are detected and utilized for determining the extent of the presence of the target cells in the examined tissue. The physical element may also be a fluorescent material which emits radiation of a predetermined frequency when illuminated by light, or a light absorption material which absorbs radiation of a particular frequency, in which cases changes in frequency of the reflected light would be detected and utilized for determining the extent of the presence of the target cells in the examined tissue.

According to further features in the described preferred embodiments, voltage pulses may be applied to a probe area of the examined tissue to detect the presence of the target cells in the probe area, and optical pulses may be applied to a central region of the probe area of the examined tissue to detect the presence of the target, e.g., cancerous, cells in the central region. Such an arrangement greatly aids the surgeon in determining, during a surgical operation, the size of a tumor to be removed, and its exact delineation from normal healthy tissue to be retained.

According to a further feature of the invention, as described below, the target cells, e.g., cancerous cells, once detected, may be subjected to optical energy of sufficient intensity to destroy them. For example, where the target cells are cancerous cells and the optical energy is laser energy, the same probe as used for detecting the cancerous cells may also be used for destroying such cancerous cells by applying femtosecond pulses at an intensity of 100 nj-1 mj at the targeted cells. Longer pulses can be also used but with more heat dissipation to the surrounding area.

According to still further features in the preferred embodiments described below, the optical pulses may be applied by means of a flexible probe introduced into a subject's body via a catheter, or incorporated in a biopsy needle.

According to another aspect of the present invention, there is provided a method of examining tissue for the present of cancerous cells therein, comprising: applying laser pulses to the examined tissue; detecting the reflections of the laser pulses from the examined tissue; comparing an optical characteristic of the laser pulses applied to the examined tissue with that of the laser reflections from the examined tissue; and utilizing the comparison of optical characteristics for determining the presence of cancerous cells in the examined tissue.

According to a still further aspect of the present invention, there is provided a method of examining tissue for the presence of cancerous cells therein, comprising: applying optical energy pulses to the examined tissue in at least two polarization forms; detecting changes in optical properties of the examined tissue in each of the polarization forms; and utilizing the detected changes for determining the presence of cancerous cells in the examined tissue.

According to a still further aspect of the present invention, there is provided a method of examining tissue for the presence of cancerous cells therein, comprising: applying voltage pulse and laser pulses to the examined tissue; detecting reflections of the voltage pulses from the examined tissue; comparing an electrical characteristic of the voltage pulse reflections from the examined tissue with that of the voltage pulses applied to the examined tissues with the laser pulses; and utilizing the comparison of electrical characteristics for determining the presence of cancerous cells in the examined tissue.

According to yet another aspect of the present invention, there is provided apparatus for examining tissue for the presence of predefined target (e.g., cancer) cells therein, comprising: a voltage pulse source; an optical pulse source; a probe having an operative end for applying optical pulses and voltage pulses from the sources to the examined tissue, and for detecting the reflections of the voltage pulses produced by the examined tissue; and a data processor system including an electrical measuring sub-system coupled to the probe for detecting changes in the electrical properties of the examined tissue produced by the optical and voltage pulses, and for determining therefrom the presence of the target cells in the examined tissue.

According to further features in the described preferred embodiments, the probe also detects optical reflections of the optical pulses from the examined tissue. In such case, the data processor system also includes an optical analyzer sub-system utilizing the detected optical reflections from the examined tissue for detecting changes in optical characteristics of the examined tissue produced by the applied pulses in determining the extent of the presence of the target cells in the examined tissue.

According to yet another aspect of the present invention, there is provided a probe for use in examining tissue for the presence of cancerous cells therein, comprising: an operative end having at least one pair of spaced conductors for applying voltage pulses to the examined tissue; and an optical fiber at the operative end for applying optical pulses to the examined tissue.

Further features and advantages of the invention will be apparent from the description below.

BRIEF DESCRIPTION OF THE DRAWINGS

The invention is herein described, by way of example only, with reference to the accompanying drawings, wherein.

Figure 1:
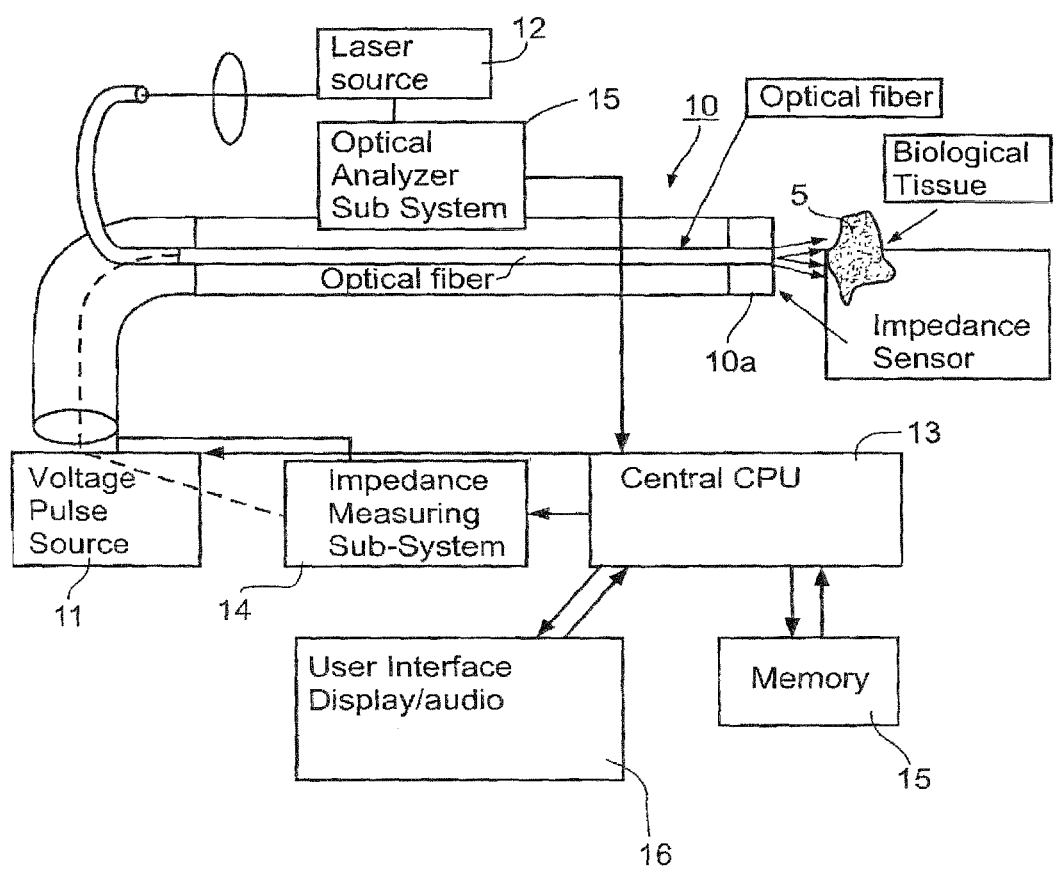
FIG. 1 is a block diagram illustrating one form of apparatus constructed in accordance with the present invention for examining tissue in a real-time manner for the presence of target cells, particularly cancerous cells, therein.

It is to be understood that the foregoing drawings, and the description below, are provided primarily for purposes of facilitating understanding the conceptual aspects of the invention and various possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

TECHNICAL DISCUSSION OF MECHANISM OF ACTION

As indicated earlier, the invention of the present application provides an electro optic method and apparatus for examining tissue for the presence of predefined target cells, particularly cancerous cells, by using the known conjugation technique presently used in imaging and drug-delivery procedures. According to the present invention, the tissue to be examined is subjected to a contrast agent containing small particles of a physical element conjugated with an antibody selectively bindable to the target cells. Energy pulses are applied to the examined tissue; and changes in impedance of the examined tissue produced by the applied energy pulses are detected; and utilizing for determining the extent of the presence of the target cells in the examined tissue.

Before describing the particulars of the method and apparatus of the present invention as illustrated in the accompanying drawings, it would be helpful first to provide a technical discussion of the conjugation technique generally and of the mechanism of action, as illustrated in FIGS. 2a-2e, involved when this technique is used in the impedance-measuring method and apparatus of the present invention for determining the extent of the presence of target (e.g., cancer cells) in an examined tissue.

One of the most promising developments in the biotechnology field is the creation of MAbs, which are exquisitely selective proteins (antigens or antibodies) that bind to only a single target. Depending on the clinical setting, the specific antigens to which MAbs may bind include bacteria, hormones, tumor cell antigens, growth factors, and a variety of other substances. The extraordinary specificity of MAbs has tremendous clinical value. As reagents, Mabs appear ideal since they are homogeneous in nature, recognize specific antigenic determinants, can be mass produced, are relatively stable to conjugation methods, and are biocompatible in vivo.

MAbs are created using cell fusion techniques in a process called hybridoma technology. Cell fusion is a form of genetic engineering that merges two types of cells to form a single cell.

First, a mouse is immunized with an antigen that specifically stimulates production of a desired antibody targeted at that antigen. White blood cells that produce antibodies, called B-lymphocytes, are isolated from the mouse's spleen. These cells are then fused to myeloma cells, which are tumor cells that replicate continuously and rapidly. Using cell fusion technology, these two cell types are merged into a single cell, called a hybridoma. The hybridoma contains the DNA of both of the original cells and thus possesses their desirable qualities.

Each hybridoma is capable of producing large numbers of identical antibody molecules, and also called MAbs because they are produced by the identical offspring of a single, cloned, antibody-producing cell. Like the lymphocytes from the immunized animal, they produce antibodies targeted at the injected antigen.

Efforts in hybridoma technology have created four different types of MAbs. Murine (mouse) MAbs have been the primary focus of MAb creation to date. However, they produce variable results. Because mouse-produced antibodies are not identical to human antibodies, they are eventually recognized as foreign proteins by the human body and cleared from circulation by human antimouse antibodies (HAMA). These reactions are not a serious problem with MAb-based diagnostic and imaging products, where only a single application may be required. However, they are a major obstacle to the therapeutic use of murine antibodies. Most patients produce a HAMA reaction, which significantly reduces therapeutic efficacy and increases toxicity.

Human MAbs do not produce a HAMA reaction, so they tend to succeed therapeutically and are less likely to produce allergic reactions. Unfortunately, it is extremely difficult to fuse human B-lymphocytes with myeloma cells. Several biotechnology companies are investigating novel ways to produce human MAbs, but this process appears to be much more expensive than murine-based systems.

Chimeric MAbs use recombinant engineering technology and involve the assembly of diverse gene segments not normally found together in nature. With this approach, recombinant genes are constructed that code for the production of specific proteins (MAbs), in which selected segments from the mouse antibody are fused to complementary segments from the human antibody. While the chimeric antibody produced retains its binding specificity, it more closely resembles a natural human antibody. Therefore, it is less likely to produce a HAMA reaction.

Humanized MAbs incorporate only the genes for the specific binding sites from the mouse.

Because MAbs act as specific probes that can be directed at the protein that induced their formation, they can be used successfully in clinical applications. For instance, MAbs can direct immune system activity by seeking out targeted antigens and attracting immune cells (such as monocytes, macrophages and lymphocytes) to the targeted cell. Additionally, MAbs can be directed at target molecules needed for cellular growth or differentiation. For example, many patients with breast cancer carry a specific protein on the surface of their tumor cells. When a MAb directed at this protein is used in combination with traditional chemotherapy, patients experience a greater degree and duration of therapeutic response. This results in a greater rate of overall survival when compared with treatment with chemotherapy alone.

Conjugated MAbs are monoclonal antibodies that are combined with some physical element like radioisotopes, toxins, metal, semiconductors or. They are also can be combined with other antibodies or drugs for targeted delivery to specific cells.

Because MAbs can be conjugated with a radioisotope, they are well suited for use in diagnosing and monitoring disease. This was one of the earliest uses for biotechnology. The first products using MAbs to diagnose disease were approved by the FDA in 1981, and MAbs have been used in diagnostic imaging since 1992. For example, in cancer diagnostics, MAbs targeted at specific antigens found on cancer cells, such as carcinoembryonic antigen, are conjugated with a radioisotope. These MAbs are then administered to patients, where they target tumor tissue when evaluated with computer tomography. This approach has been successful in diagnosing and monitoring patients with colorectal, ovarian and prostate cancers.

As indicated earlier, in the present invention such a technique is used (e.g., with a non-radioactive conjugated antibody) in an impedance measuring procedure for detecting cancer cells.

FIGS. 2a-2e schematically illustrate the process of producing the conjugated MAbs, namely a physical element conjugated with an antibody selectively bindable to certain defined target cells, such as cancer cells; and the manner in which such MAbs, when included in a contrast agent applied to the tissue to be examined, affect the impedance measurement of such tissue to provide all indication of the extent of the presence of the target (e.g., cancer) cells in such examined tissue.

Figure 2A:
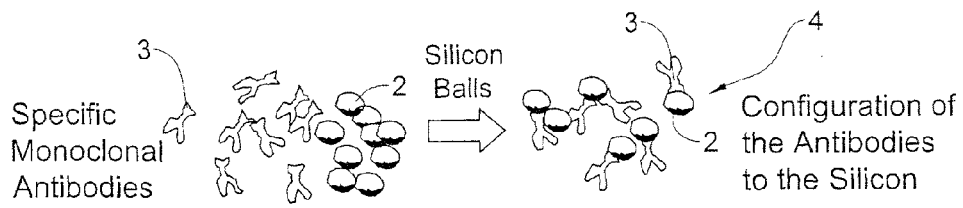
FIGS. 2a-2e are pictorial illustrations illustrating the mechanism of action involved in the impedance measuring technique of the present invention, when using a contrast agent conjugated with an antibody selectively bindable to the cancerous cells.

FIG. 2a illustrates the conjugation process generally, wherein small particles (of nanometer or micrometer size, and therefore hereinafter termed "nano/micro-particles) of a physical element 2, such as silicon nano/micro-particles, are conjugated with a specific monoclonal antibody 3, selectively bindable to the target cells in the tissue to be examined, to produce a conjugation of the antibodies to the silicon nano/micro-particles, as shown at 4.

Figure 2B:
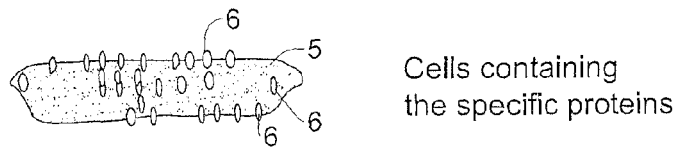

FIG. 2b illustrates a cancer cell 5 containing specific proteins 6 on its cell membrane to which the monoclonal antibodies 3 are selectively bindable or attachable.

Figure 2C:
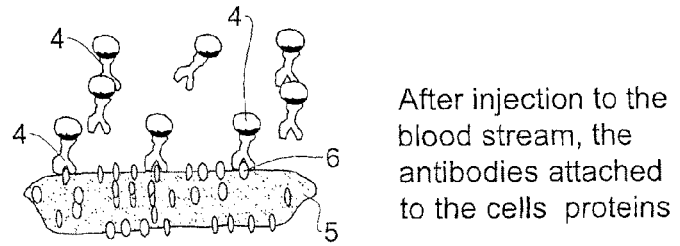

FIG. 2c illustrates the attachment process occurring when the conjugated physical elements 4 of FIG. 2a are included in a contrast agent injected into the blood stream of the tissue 5 to be examined, so that the conjugated elements 4 attach to the specific proteins 6 in the cell 5. It will thus be seen that, because of the high bonding selectivity of the monoclonal antibodies 3 of the conjugated silicon particles 4 with respect to the specific proteins 6 within the cancer cell 5, tissue having such cancer cells will have a concentration of such nano/micro-particles bonded thereto in proportion to the number of cancer cells, whereas tissue not having cancer cells will not have such nano/micro-particles bonded thereto.

Accordingly, the extent of the presence of cancer cells in the examined tissue will be indicated by the extent to which the conjugated nano/micro-particles 4 have been bonded to the tissue. The extent of the presence of cancer cells in the examined tissue can thus be determined by measuring the impedance, or changes in impedance, of the examined tissue.

Figure 2D:
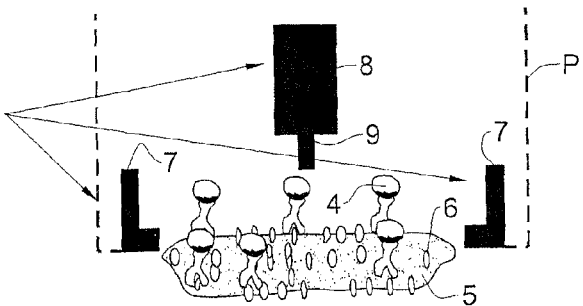

FIG. 2d schematically illustrates making such an impedance measurement of the examined tissue 5 in order to determine the extent of the target cells therein. Preferably in accordance with the present invention, the nanoparticles 2 conjugated with the antibodies 3 are particles which change in impedance when illuminated by optical energy, particularly laser energy. Thus, when the nano/micro-particles 2 are of a semiconductor, such as silicon, silicon absorbs light photons above 1.1ev and produces a substantial increase in conductivity by transferring electrons from the valance band to the conduction band.

In order to exploit this substantial change in the impedance of the examined tissue for purposes of determining the extent of cancer cells therein, an electro-optical probe, generally designated P in FIG. 2d, applies both optical pulses and voltage pulses to the examined tissue 5. In a preferred described embodiment, the voltage pulses are applied by a pair of coaxial conductors 7, 8 at the operative end of the probe, and the optical pulses are laser pulses applied via an optical fiber 9 extending through the inner conductor 8.

Figure 2E:
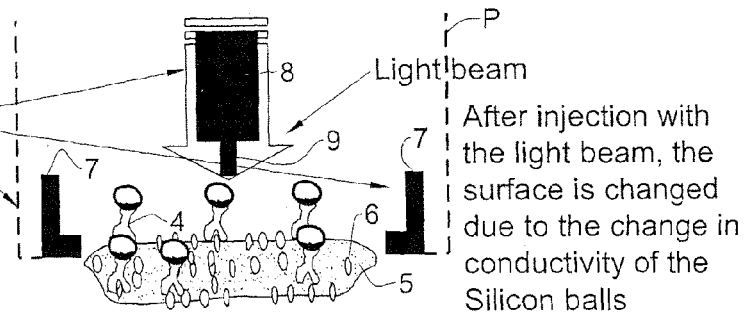

FIG. 2d schematically illustrates the situation when the examined tissue 5 is not subjected to the laser, in which case the impedance of the examined tissue would be relatively high; whereas FIG. 2e illustrates the situation when a light beam is applied via optical fiber 9 to the examined tissue 5, in which case the impedance of the tissue would be substantially decreased.

FIGS. 2d and 2e illustrate a further important feature of the present invention, namely that the voltage pulses produced by the electrode 7, 8 are applied to a relatively large probe area of the examined tissue to detect the extent of the presence of cancer cells in the probe area; whereas the optical pulses from optical fiber 9 are applied to a central region of the probe area of the examined tissue to detect the extent of the presence of cancer cells in the central region. This feature enables the probe to detect, with relatively high accuracy, any cancer cells within the probe area, as shown by the following example:

EXAMPLE

Let us assume that the area of the electrical probe P is 160μ×160μ, that silicon conjugated crystals are joined to cancerous cells at that probe area, and that there are about 16 cancerous cells on the surface of that probe area. On each cell there are many thousands of 10 to 100 nm diameter silicon crystals; (in this example we are using the electrical parameter of the bulk material; the exact electrical parameters will be different for the various sizes of the crystals from the nanometer size to the micrometer size). The conductivity [=1/resistivity] of normal cells is, for example, 0.02-0.05 S/m for fat tissue, 0.1 S/m for brain tissue, and 1.3 S/m for saline. Normal tissues of the above dimension will have a resistance of about $10^8$ Ω for fat, $7.5\times10^5$ Ω for saline, and $10^4$ Ω for brain tissue. The resistance of the probing zone is given by:

$$R=\rho \times L/[w\times d].$$

where: ρ is the resistivity, L is the sample length, w is the sample width, and d is the thickness of the layer.

When light irradiates the sample, the resistivity of the crystal is reduced from about 1 KΩcm to about $10^{-6}$ Ω cm, and the resultant resistance will be about 1 Ω? to 0.1 Ω? It is clear that the change is dramatically large. This abrupt change will be detected by the impedance measurements, as well as by light reflection, as described below.

Assuming only one cancerous cell exists between those 16 cells, and the one cell is only partially covered with silicon crystal, even with a covering ratio of 1/1000the total change can be easily detected using a lock-in method, as also described below.

Following is a simplified order of magnitude calculation.

1 cell: 40 μm×40 μm=1600 μm$^2$=1600×$10^6$ nm$^2$ 1 average silicon crystal: 40 nm×40 nm=1600 nm$^2$ Assuming only $10^3$ crystals on one cell, the covering ratio is 1600 nm$^2$×$10^3$/1600×$10^6$ nm$^2$=$10^{-3}$; and the probe area is 160 mm×160 mm for about 16 cells. If only one cell is cancerous, the effective covering ratio is $10^{-3}$/16. The change in conductivity of each crystal is of the order of $10^4$. Therefore one cell among 16 normal cells will induce $10^4\times10^{-3}$/16~0.5 change in conductivity averaged over the 16 cells area. Even if the noise is of the order of 1000 times greater than the signal, by using a lock-in method, as described more particularly below, the signal is well in the detectable region.

DETAILED DESCRIPTION OF PREFERRED EMBODIMENTS

The Embodiment of FIG. 1

The apparatus illustrated in FIG. 1 includes an electro-optical probe, generally designated 10, having an operative end 10a for applying optical pulses and voltage pulses to tissue 5 to be examined. The illustrated apparatus further includes a voltage pulse source 11 and a laser source 12 coupled to the probe 10 for applying voltage pulses and optical (laser) pulses, respectively, to the examined tissue 5. Probe 10 also detects reflections of the voltage pulses and of the optical pulses from the examined tissue 5.

The illustrated apparatus further includes a central data processor system 13; an impedance measuring sub-system 14 coupled to the probe for detecting the impedance of the examined tissue and the change of impedance by the optical pulses; and an optical analyzer sub-system 15 for detecting changes in the optical characteristics of the examined tissue produced by the applied optical pulses. As described above with reference to FIGS. 2a-2e, and as will be described more particularly below, the detected changes in impedance and in the optical characteristics of the examined tissue 5, as a result of having been subjected to a contrast agent containing small particles of a physical element conjugated with an antibody selectively bindable to cancerous cells, provides an indication of the extent of the presence of cancerous cells in the examined tissue.

The apparatus illustrated in FIG. 1 further includes a memory unit 15 for storing pre-prepared data, as well as data produced during the operation of the apparatus. The apparatus further includes a user interface 16 for producing a display output and/or an audio output during the operation of the apparatus.

The impedance measuring sub-system 14 is preferably that described in my above-cited U.S. application Ser. No. 10/035,428. In such a system, the electro-optical probe 10 applies the electrical pulses to the tissue 5 being examined such that the probe generates an electrical fringe field in the examined tissue and produces reflected pulses therefrom with negligible radiation penetrating into neighboring tissues near the examined tissue. The reflected electrical pulses are detected, and their electrical characteristics are compared with respect to the applied electrical pulses, to measure the impedance of the examined tissue relative to the impedance of its neighborhood and by comparison to find similarities to the pre-recorded data.

Such electrical property measurements, involving the complete area of the examined tissue contacted by the operative end of the probe 10, are capable of distinguishing between fat, muscle, bone, cancerous tissue and other human tissue, and therefore can serve to guide the surgeon on the way to the tumor and to define the tumor margin with a typical accuracy of about 90%. The optical beam produced by the laser 12 is applied to the center region of the probe area, and is capable of detecting, with much better accuracy, cancerous cells conjugated to the physical particles at the central region.

Preferably, the small particles are nano/micro-particles in size and are of a light-sensitive semiconductor, such as Silicon Germanium or CdTe crystals, having a conductivity that substantially decreases in the presence of light. While the use of a light-sensitive semiconductor is particularly advantageous, as described more particularly below, other materials can be used for the nano/micro-particles conjugated with the antibody For example, nano/micro-particles of a metal, such as gold, having good reflecting characteristics can be used, whereupon an optical characteristic (e.g., amplitude, frequency or phase) of the reflected light could also be detected and utilized for determining the extent cancerous cells are present in the examined tissue. The nano/micro-particles may also be of a fluorescent material, which emits radiation of a predetermined frequency, such as fluorescent dye Hoechst 33258 which emits light at 470 nm when exited at 360 nm, or a semiconducting-fluorescent material like CdSe and Cds could be of a light absorption material which absorbs radiation of a particular frequency, such as diamond nanoparticles which absorbs radiation of from 200 to 700 nm, or CdSe and Cds. The emission wavelength of a nanocrystal depends on its size, and therefore by controlling its size, it is possible to tune the emission wavelength. The excitation spectrum of nanocrystals is very broad. This has the advantage that nanocrystals can be excited at many wavelengths shorter than the emission peak. It further means that a mixture of nanocrystals with different emission peaks may be excited efficiently by light of a single wavelength. Therefore, the numbers set forth above can be tuned and adjusted.

In the above cases, changes in the spectrum of the reflected light would be detected and utilized for determining the extent cancer cells are present in the examined tissue.

Another possible application of the invention would be to use nano/micro-particles of a dielectric material, such as Iodine (which has a large dielectric constant (about 120), and to apply only voltage pulses, in which case the optical analyzer sub-system could be omitted or not used, and only the impedance measuring sub-system would be used for measuring the impedance of the examined tissue.

The Apparatus of FIGS. 3-8

The apparatus of FIGS. 3-8 also includes an electro-optic probe 20 having an operative end 20a for applying optical pulses and voltage pulses to tissue 5 to be examined, and for detecting both voltage reflections and optical reflections of such pulses in order to determine the extent cancerous cells are present within tissue 5. As indicated earlier, such an examination is made after the tissue has been subjected to a contrast agent containing small particles (nano/micro-particles) of a physical element conjugated with an antibody selectively bindable to the cancerous cells.

Figure 3:
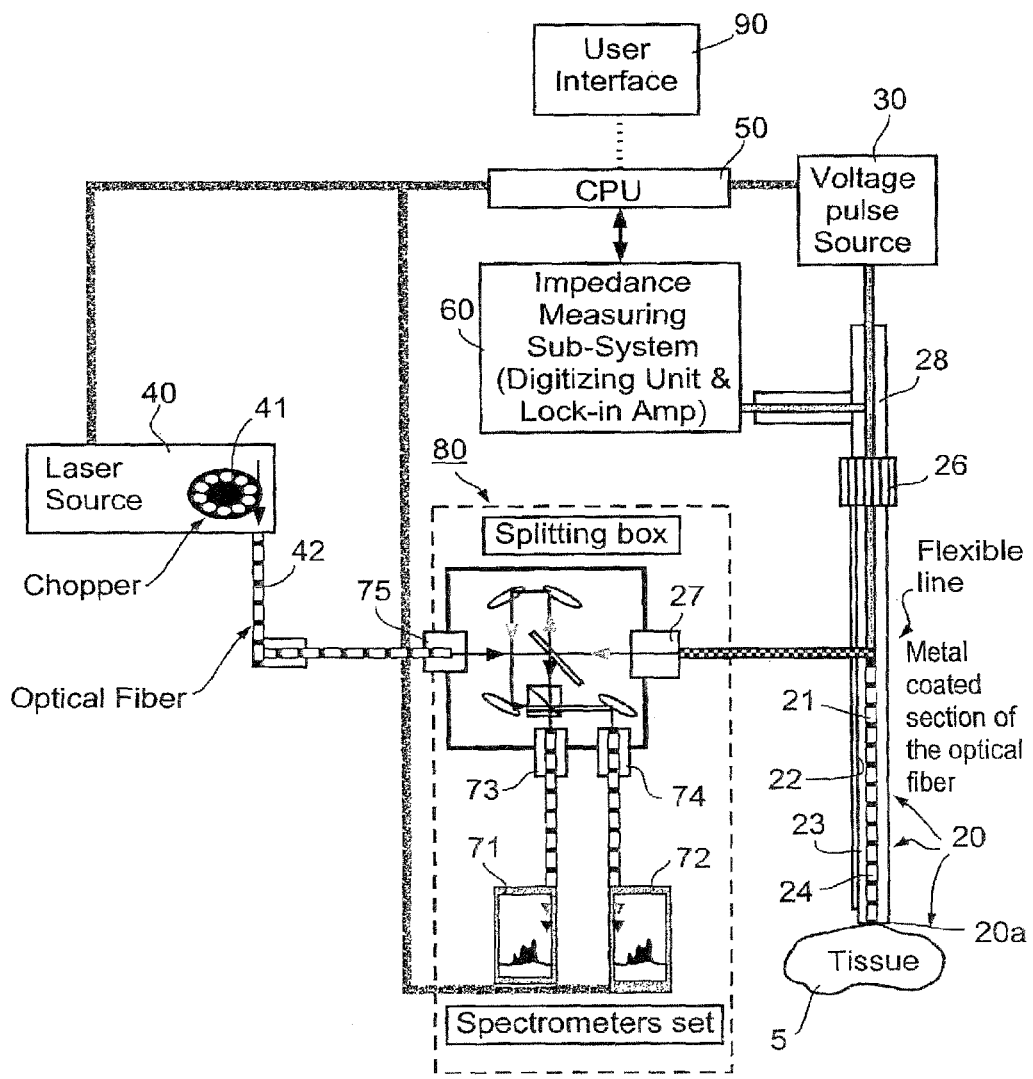
FIG. 3 is a block diagram illustrating a second form of apparatus constructed in accordance with the present invention.

The voltage pulses are applied from a voltage pulse source 30, and the optical pulses are applied by a laser 40 via an optical chopper 41 and an optical fiber 42. The illustrated apparatus further includes a data processor system, generally designated 50, having an impedance measuring sub-system 60. Data processor system 50 further includes an optical analyzer sub-system, generally indicated by the broken-lines 70, having a light splitting box 80. Further illustrated in FIG. 3 is a user interface 90, which includes a visual display as well as an audio output.

Figure 4:
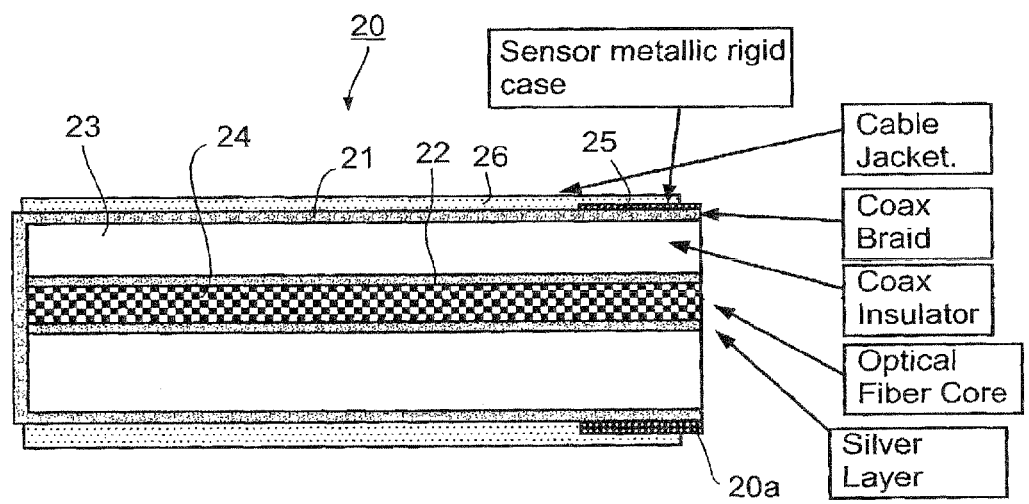
FIG. 4 illustrates generally the construction of the electrical properties probe in the apparatus of FIG. 3.
Figure 10:
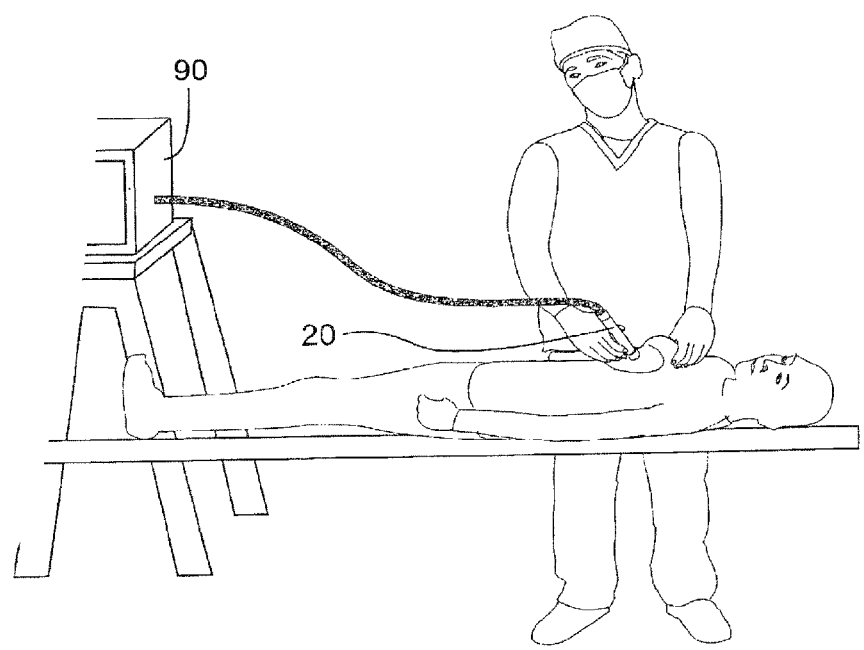
FIG. 10 is a pictorial illustration illustrating the manner of using the apparatus of FIG. 3 for detecting cancer cells in a real-time manner during a surgical operation for removing a tumor.

The electro optic probe 20 is more particularly illustrated in FIG. 4. It is in the form of an elongated member adapted to be grasped by the surgeon during a surgical operation for the removal of a tumor, as shown in FIG. 10, with its operative end 20a brought into direct contact with the tissue at the surgical site.

Probe 20 is preferably of a construction similar to the electrical probe described in my above-cited patent application Ser. No. 10/035,428, to include outer and inner coaxial conductors 21, 22 insulated from each other by a body of dielectric material 23, for generating an electrical fringe field in the examined tissue as described in that patent application.

Figure 5:
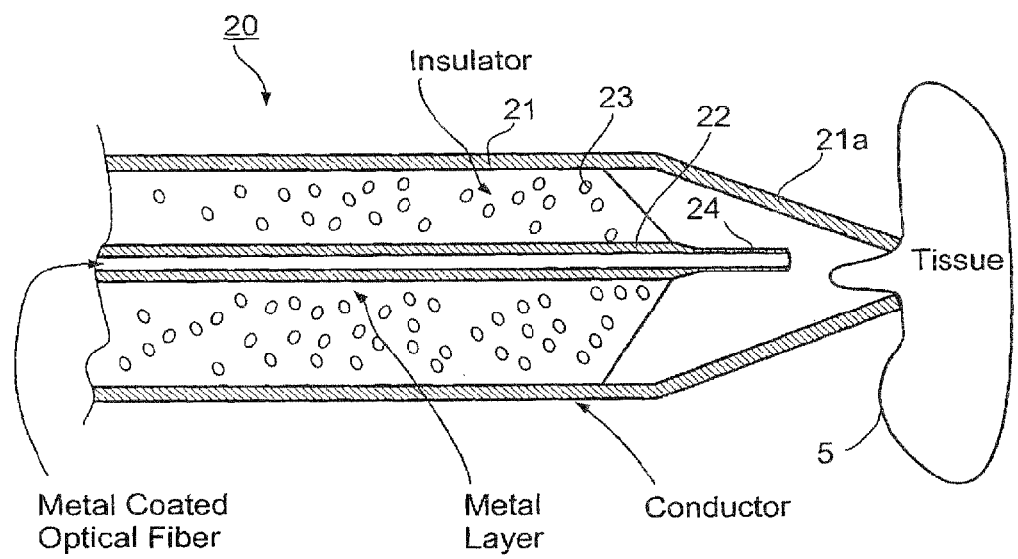
FIG. 5 illustrates a preferred construction of the operative end of the probe of FIG. 3.

Probe 20 illustrated in FIG. 4, however, further includes an optical fiber 24 extending centrally through the probe to conduct optical pulses from laser 40 to the examined tissue in the central region of the tissue area covered by the operating end 20a of the probe. As schematically shown in FIG. 5, the outer conductor 21 is preferably tapered at the operative end of the probe to provide a tapered tip 21a. it also extends slightly past the respective end of the inner conductor 22, as well as of the central optical fiber 24, to define an open cavity closed by the tissue 5 being examined.

The inner conductor 22 is preferably a silver or other metal coating over the outer surface of the central optical fiber 24 whereas the outer conductor 21 is preferably in the form a flexible metal braid. At the operative end of the probe, the outer conductor 21 is enclosed by a rigid metal cap 25. The complete outer surface of the outer conductor 21, including its cap 25, is preferably covered by an insulating jacket 26.

As described above, the two coaxial conductors 21, 22 apply voltage pulses from the voltage source 30 to the examined tissue 5, whereas the central optical fiber 24 applies optical pulses from the laser 40 to the central region of the probe area. The voltage pulses produce voltage reflections, and the optical pulses produce optical reflections, both of which are detected by the probe 20.

Figure 6A:
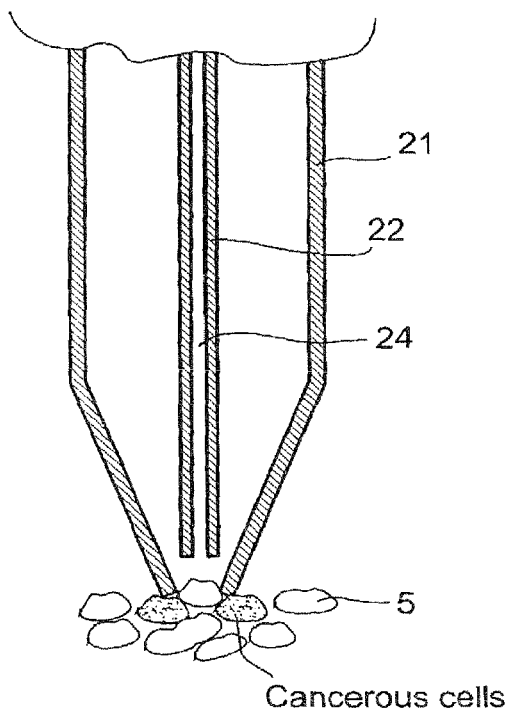
FIG. 6a illustrates the probe of FIG. 9 when examining tissue constituted only of normal cells.
Figure 6B:
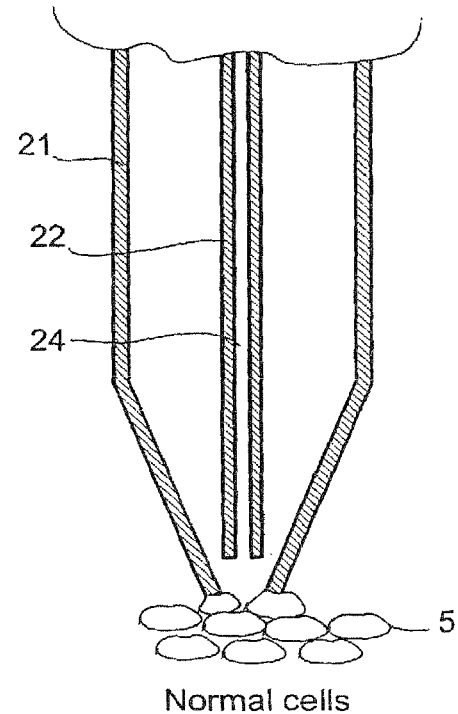
FIG. 6b illustrates the probe of FIG. 5 when examining tissues including cancerous cells.

FIGS. 6a and 6b schematically illustrate the results produced by such an examination with respect to tissue that has been previously subjected to a contrast agent as described above, namely one containing small particles (nano/micro-particles) of a physical element, particularly a light-sensitive semiconductor such as silicon, conjugated with an antibody selectively bindable to cancerous cells. Thus, when the examined tissue contains cancerous cells, the physical element nano/micro-particles are bonded to the cells, according to the extent the cancerous cells are present in the examined tissue, as shown in FIG. 6a; whereas examined tissue not containing cancerous cells are relatively free of such physical element nano/micro-particles, as shown in FIG. 6b.

Figure 7:
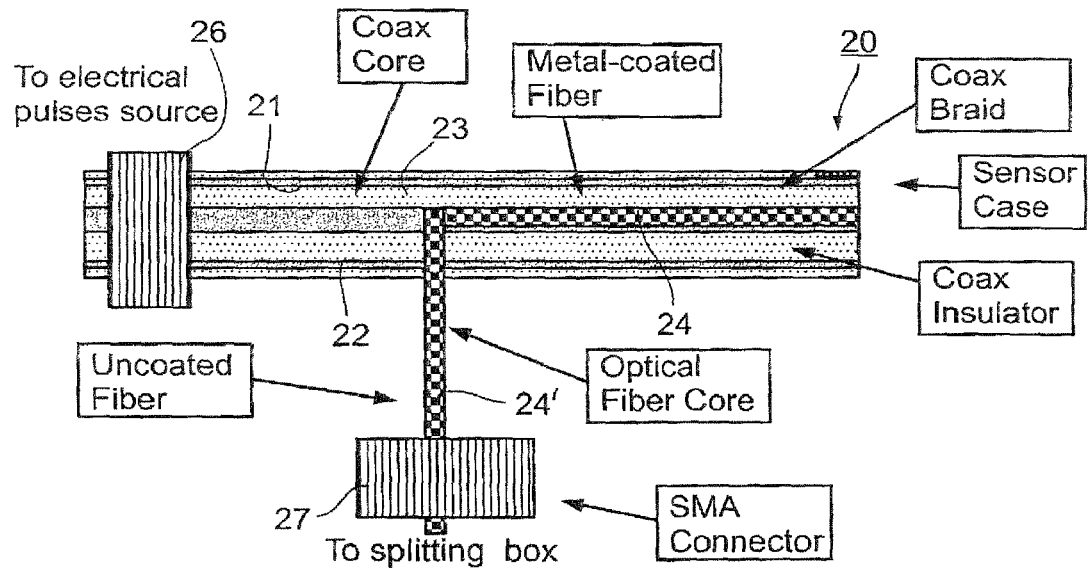
FIG. 7 schematically illustrates the probe in the apparatus of FIG. 3 and its connections to the impedance measuring and optical analyzer sub-systems.

As shown in FIG. 7, and also in FIG. 3, the inner and outer conductors 21, 22 of the probe are connected by a connector 27, e.g., an SMA connector, to the voltage pulse source 30. The central optical fiber 24 is passed through an opening in the inner conductor 22 and outer conductor 21 to its external extension 24' which includes a connector 27, e.g., an SMA connector, for connection to the laser source 40.

As shown in FIG. 3, the coaxial conductors 21, 22 of the probe 20 are connected, via connector 26 and a transmission line 28, to the voltage pulse source 30, and to the impedance measuring sub-system 60. The voltage pulse source 30, and the impedance measuring sub system 60, are basically the same as described in the above-cited patent application Ser. No. 10/035,428, except that the impedance measuring subsystem includes a lock-in amplifier locked-in with chopper 41 of the laser source 40, to increase the signal-to-noise ratio of the impedance measurement by measuring the mutual optical-electrical effect (mode 3), as will be described more particularly below.

The laser source 40 produces a sequence of femtosecond to nanosecond pulses of viz-nir (Visible-Near Infra-Red) light (the duration of the laser pulse is controlled by the CPU). Laser source 40 further includes an optical chopper 41 for chopping the train of nanosecond pulses at a desired frequency or modulation. The chopping modulation could be a constant modulation, for example 1000 HZ modulation, or other kind of modulation for example information-like modulation. The chopper itself is a standard mechanical chopping device (or an electro optic device) and is mounted inside the laser source box 40. As one example, chopper 41 could be Model 360C OEM Ultra Miniature Optical Chopper made by Sciatic Instruments Ltd. As seen in FIG. 3, the train of laser pulses exiting from chopper 41 are transmitted, via an optical fiber 42 and optical splitting box 80 of the optical analyzer sub-system 70, to the external extension 24' of optical fiber 24 within the probe 20.

As further shown in FIG. 3, the optical analyzer sub-system 70 includes two spectrometers 71, 72, each coupled by a separate connector 73, 74 to the optical splitting box 80. The optical splitting box 80 is more particularly described below with respect to FIG. 8. As further shown in FIG. 3, optical fiber 42 includes another connector 75 connecting the chopped laser pulses from laser source 40 to the optical splitting box 80 for transmission therethrough to the optical fiber 24 within probe 20, via connector 27 and external extension 24' of the optical fiber.

Figure 8:
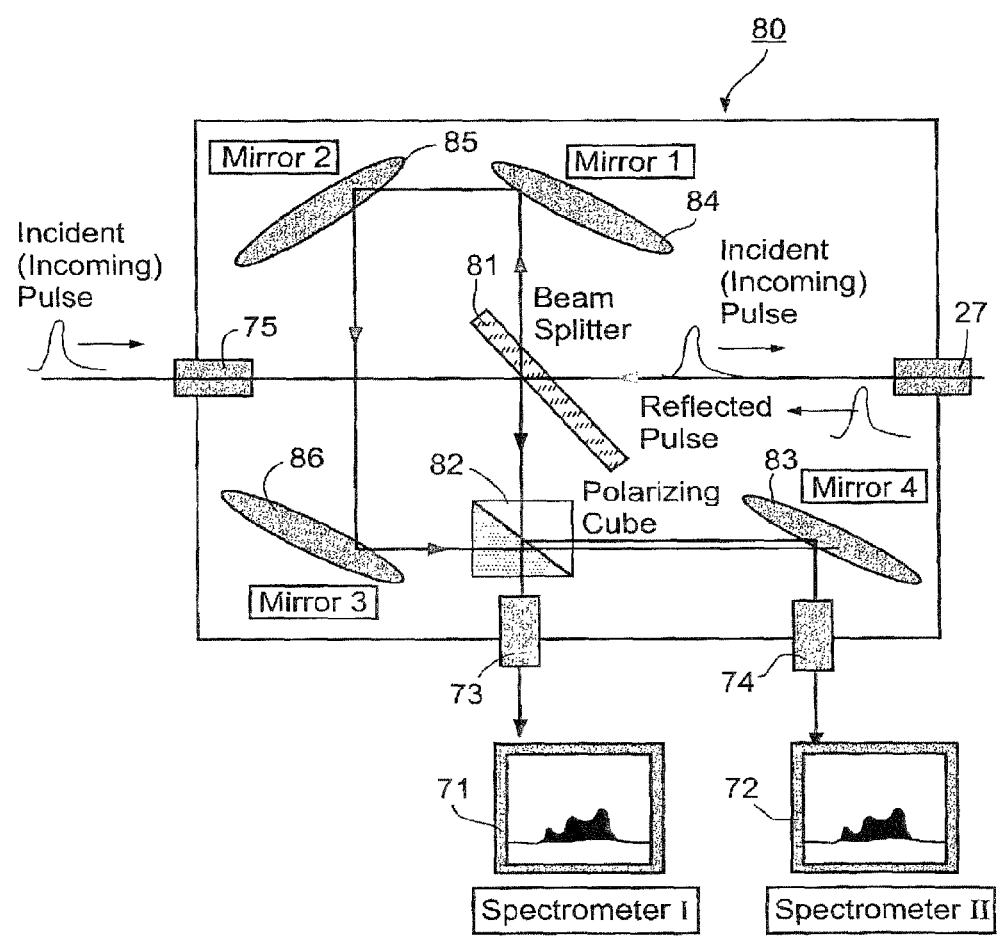
FIG. 8 illustrates the optical splitting box in the optical analyzer sub-system of FIG. 3.

FIG. 8 more particularly illustrates the optical splitting box 80, including its connector 75 to the laser source 40, its connector 27 to optical fiber 24 within probe 20, and its connector 73 and 74 to the two spectrometers 71, 72.

As shown in FIG. 8, the optical splitting box 80 includes a beam splitter 81 which splits the beam of laser pulses from laser 40 and chopper 41 into two beams: a main beam, carrying most of the laser energy, is directed to optical fiber 24 in the probe, via connector 27 and the external extension 24' of the optical fiber; whereas a secondary beam is directed to a polarizing cube 82. Polarizing cube 82 splits the secondary beam into two differently polarized beams, one being directed via connector 73 to spectrometer 71, and the other being directed by mirror 83 and connector 74 to spectrometer 72. As will be described below, this arrangement including polarizing cube 82 and the two spectrometers 71, 72 measures the spectrum of the incident optical (laser) pulses at each polarization separately.

The light reflected back from the examined tissue is detected by optical fiber 24 and is directed, by its extension 24' and connector 27, to the backside of beam splitter 81. This reflected light is in turn reflected by beam splitter 81, via mirrors 84, 85 and 86, to the polarizing cube 82. Cub 82 again splits the reflected light according to two polarizations, one being passed via connector 73 to spectrometer 71, and the other being passed via mirror 83 and connector 74 to the other spectrometer 72.

The two spectrometers 71, 72 thus measure the frequency spectrum of both the incident optical pulses and reflected optical pulses at each polarization. As will be described more particularly below, this information is also utilized, in addition to the impedance-measurement information, in determining the extent the cancerous cells are present in the examined tissue.

Figure 9A:
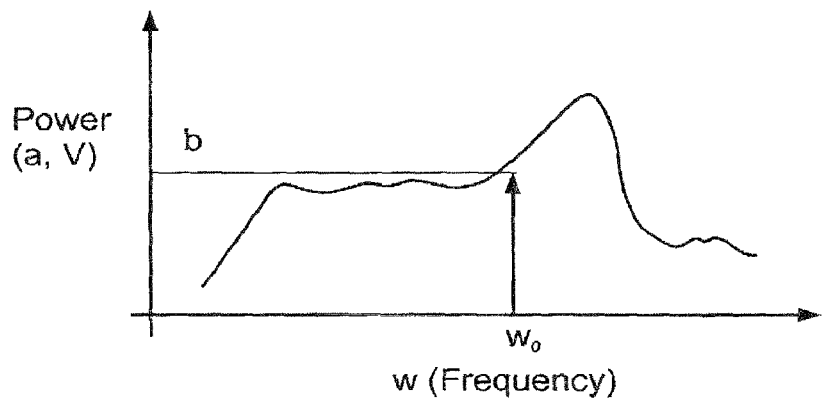
FIGS. 9a and 9b illustrate examples of polarization measurements from the two spectrometers in the optical analyzer sub-system of FIGS. 3 and 8.
Figure 9B:
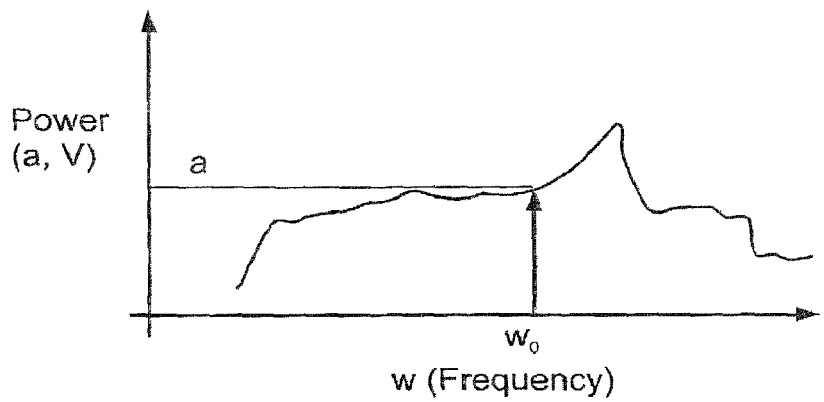

Each spectrometer 71, 72 is a fiber optic spectrometer equipped with computer software that allows real-time detection of optical properties of the light directed into the spectrometer, namely a portion of each incident optical pulse, and all of each reflected pulse. As one example, each spectrometer may be Ocean Optic pc2000 fiber optic spectrometer or Wavestarv750 made by Ophir. The main spectrometer reading is the power spectrum of the light (amplitude at each optical frequency). Both spectrometers are preferably the same. FIGS. 9a, 9b illustrate typical outputs of the two spectrometers 71, 72 during a typical examination procedure.

The optical fiber 24 may be a commercial Silica core silica clad fiber, optimized for the NIR-VIZ (near infrared, visible light range of the electromagnetic spectrum). The outer diameter of the fiber is preferably 45 μm.

Following is one manner of making the electro-optical-probe 20.

A length of the commercially available optical fiber 24 is coated with a silver layer to define the inner conductor 22, is then covered with a thick dielectric layer, preferably Teflon™, and is inserted into the flexible metal braid serving as the outer conductor 21 of the coaxial cable so produced. A metal rigid cap 25 is then applied at one of the coaxial cable, constituting the operative end of the probe to be produced, and a thin layer of a polymer is then applied over the coaxial cable to serve as the outer jacket 26.

In view of the flexible nature of the probe, the metal cap facilitates grasping and moving the probe by the surgeon. As one example, the metal cap may be a gold-coated aluminum cylinder of 8 mm in length.

The optical fiber 24 is split into two portions; at the opposite end of the probe. One portion coated with the inner conductor 22 continues to the opposite end of the probe where it is connected, together with the outer conductor 21, to connector 26 for connection, via transmission line 28 (FIG. 3), to the voltage pulse source 30 as well as to the impedance measuring sub-system 60. The other part of optical fiber 24 is passed through an opening in the outer conductor braid 21, and serves as the external extension 24' of the probe and carries connector 27 for connection, via the optical splitting box 80 described above, to the laser source 40.

Transmission line 28, illustrated in FIG. 3, may be a standard coaxial cable such as the RG-174, with the inner conductor constituted of a silver coating applied to the outer surface of the optical fiber 24.

The impedance-measuring method performed by the impedance measuring sub-system 60 in FIG. 3 is preferably basically the same as in my above-cited U.S. patent application Ser. No. 10/035,428, the contents of which are incorporated herein by reference. In this case, however, the impedance measurement is affected by the type of nano/micro-particles selectively bonded to the cancerous cells of the examined tissue, and the extent to which such nano/micro-particles have been bonded. The latter factors thereby provide an indication of the extent of the cancerous cells present in the examined tissue.

For example, if the nano/micro-particles are merely particles of dielectric material, then the extent to which they have become bonded to the examined tissue will merely affect the impedance of the examined tissue. However, if such nano/micro-particles are light-sensitive such that their impedance is of one value in the absence of light, and another value in the presence of light, then the presence of light pulses from the laser 40 will also affect the impedance of the examined tissue. Therefore the light can modulate the impedance of the tissue. The ability to modulate the measured impedance, only of cancerous tissue, is what make this mode so powerful. In the preferred embodiment of the invention, the nano/micro-particles are preferably of a semi-conductor crystal, e.g., silicon, exhibiting a very substantial increase in electrical conductivity when exposed to light.

The Lock-In Method

As indicated earlier, laser source 40 includes a chopper 41, and the impedance measuring sub-system 60 includes a lock-in amplifier. These features enable a lock-in examination to be performed to increase the sensitivity of the measurement particularly with respect to background noise. Thus, the lock-in measurement method can provide high-resolution measurements producing relatively clean signal outputs having a high signal-to-noise ratio over several orders of magnitude and frequency.

A lock-in amplifier, commonly used with most AC indicating instruments, provides a DC output proportional to the AC signal under investigation. In practice, the DC output may be presented as a reading on a digital panel meter or as a digital value communicated over a computer interface, rather than a voltage at an output connector, but the principle remains the same. A special rectifier, called a phase-sensitive detector (PSD), which performs this AC to DC conversion, forms the heart of the instrument. It is special in that it rectifies only the signal of interest, while suppressing the effect of noise or interfering components, which may accompany that signal.

The traditional rectifier in a typical AC voltmeter makes no distinction between signal and noise and produces errors due to rectified noise components. The noise at the input to a lock-in amplifier, however, is not rectified but appears at the output as an AC fluctuation. This means that the desired signal response, now a DC level, can be separated from the noise accompanying it in the output by means of a simple low-pass filter. Hence in a lock-in amplifier, the final output is not affected by the presence of noise in the applied signal.

In order to function correctly, the detector must be "programmed" to recognize the signal of interest. This is achieved by supplying it with a reference voltage of the same frequency and with a fixed phase relationship to that of the signal. This is most commonly done by ensuring that they are derived from the same source. The use of the reference frequency ensures that only signals at the reference frequency will be measured. In our case the reference frequency is given by the optical modulation frequency so the impedance changes in the tissue are in the reference frequency while all other "noises" are not in that frequency. This inherent tracking ability allows extremely small bandwidths to be defined for the purpose of signal-to-noise ratio improvement since there is no frequency "drift", as is the case with analog "tuned filter/rectifier" systems. Because of the automatic tracking, lock-in amplifiers can give effective "Q" values (a measure of filter selectivity) in excess of 100,000, whereas a normal band pass filter becomes difficult to use with Q's greater than 50.

The following mathematical description of a typical lock-in operation will aid in understanding this measurement method.

Consider the case where a noise-free sinusoidal signal voltage Vin is being detected, where Vin=A cos (ωt) ω is the angular frequency of the signal which is related to the frequency, F, in Hertz by the equality: –ω=2πF.

The lock-in amplifier is supplied with a reference signal at frequency F derived from the same source as the signal, and uses this to generate an internal reference signal of: –Vref–B cos (ωt+q). The reference frequency is the modulation frequency of the optical chopper, where q is a user-adjustable phase-shift introduced within the lock-in amplifier.

The detection process consists of multiplying these two components together so that the PSD output voltage is given:

by:–Vpsd=A cos (ωt).B cos (ωt+q)=½AB cos θ½Abcos (2ωt+q)

If the magnitude, B, of the reference frequency is kept constant, then the output from the phase-sensitive detector is a DC signal which is:

Proportional to the magnitude of the input signal A

Proportional to the cosine of the angle, q, between it and The reference signal

Modulated at 2ωt, i.e., it contains components at twice the Reference frequency.

The output from the PSD then passes to a low-pass filter which removes the 2ωt component, leaving the output of the lock-in amplifier as the required DC signal.

In a practical situation the signal will usually be accompanied by noise, but it can be shown that as long as there is no consistent phase (and therefore by implication frequency)

relationship between the noise and the signal, the output of the multiplier due to the noise voltages will not be steady and can therefore be removed by the output filter that integrates the signal over a time interval. The out of phase components which contains the noise will be summed towards zero, while the in phase signal will be summed.

Thus, a condition in the use of the lock-in measurement method is that the detected signal should be modulated at a reference frequency while all other signals from the surrounding environment should not be modulated. This condition is satisfied in above described method and apparatus by providing modulation to the physical element conjugated to the antibody. In all other respects, the lock-in method used herein is the same as in traditional lock-in measurements.

A preferred amplifier in the impedance measuring subsystem 60 is the commercial Lock-In Model SRS850.

Examination Procedure

FIG. 10 illustrates a typical examination procedure for examining a patient in order to determine the extent of the presence of cancerous cells in examined tissue during a surgical operation for removing a tumor.

Before the surgical operation, the contrast agent is prepared and injected into the patient's bloodstream. As described above, the contrast agent includes a tumor specific antibody conjugated to nano/micro-particles of a physical element having a characteristic which affects the impedance measurements of the examined tissue, and preferably also of the optical measurements of the examined tissue.

The present invention integrate synergistically two modalities in the same device: (1) local electrical measurement, and (2) optical detection. Both modalities can work independently to detect the existence of cancerous tissue, or together, in conjunction with a pre-injected contrast agent to detect, with high accuracy the cancerous cells. The contrast agent consists of antibodies conjugated to small particles, or nano/micro-particles, of physical elements. The synergetic combination of the two detection technologies allows the following three detection Modes of operation, depending on the material used for the nano/micro-particles and one cell destruction mode (Mode 4):

1. Electrical measurement only;
2. Light reflection measurement only;
3. Light induced impedance change measurement, preferably, also with light-reflection measurement.

Thus, if the nano/micro-crystals are merely non-switchable material like a dielectric or a conductor material, such as Iodine or gold, the extent of their presence in the examined tissue would affect the impedance of the examined tissue, in which case merely an impedance measurement may be made of the examined tissue to provide an indication of the extent cancerous cells are present therein. In the case of iodine, the measurement will detect its impedance because of the high dielectric constant of the iodine. In the case of gold, the measurement will detect the very low conductivity of the gold particles. Such an examination may be called a Mode 1 examination.

On the other hand, if the nano/micro-particles are of a light-reflecting material, such as nano/micro-particles of gold or of a light fluorescent material, such as CdSe, Cds, or of a light absorptive material such as diamond nano particles, an optical examination and analysis of the light detected from the examined tissue would also provide an indication of the extent cancerous cells are present in the examined tissue. Such an examination may be called a Mode 2 examination.

Preferably, however, the nano/micro-particles are light sensitive, such as Silicon, Germanium, ZnSe, ZnS or GaAs crystals, which substantially affect the impedance of the examined tissue when irradiated with light (e.g., laser pulses). When such materials are used as the nano/micro-particles, a Mode 3 type examination may be performed. In this mode any sequence of light pulses will induce a similar sequence of impedance-change pulses. Since the light pulses are controllable, the changes in the impedance pulses can be expected. This knowledge regarding the impedance modulation is used to improve the signal-to-noise ratio of the system.

While the first two modes can be measured, in principle, sequentially by two different devices, the third mode is a unique one and can be realized only with a device that combines the 1 and 2 modalities. The ability to control cells impedance using light, switching on and off, make this mode an enabling tool for ultra-high accuracy tumor cells detection.

It will be appreciated that the contrast agent could include just one of the above-type nano/micro-particles conjugated with the tumor-specific antibody, or could include a plurality of such types of nano/micro-particles, to permit more than one of the above mode-type examination to be performed on the tissue. Furthermore a few different types of nanocrystals can be attached together to form a microsphere.

Accordingly, during the course of a surgical operation for the removal of a tumor, the surgeon may move the probe 20 over different tissues in order to examine such tissue to determine the extent of cancerous cells therein, and thereby to decide whether such tissue should be considered as cancerous tissue to be removed, or healthy tissue not to be removed. As the surgeon moves probe 20 to different tissues of the patient's body, the data processor system housed within the user interface unit 90 shown in FIG. 10 examines the tissue and provides a visual display and/or audio signals corresponding to the results of the examination of the specific tissue. For example, the tissue type and dielectric properties may displayed on the user interface 90 such that when a cancerous cell is detected, the surgeon hears a sharp tone from the user interface.

The broad determination of tissue type by electrical properties measurement, and the accurate detection of cancerous cells by physical element detection, gives the surgeon excellent background knowledge for decision-making during the operation as to the delimitation of the cancerous tissue. Using that knowledge, the surgeon can manipulate the surgical cutting tool to maximizing the removal of cancerous tissue and minimize the removal of healthy, non-cancerous tissue.

In the embodiment of the invention described below, the nano/micro-particles are of a light-sensitive semi-conductor, such as silicon, which drastically changes in impedance when exposed to light immediately after absorbing the light. In addition, both optical (laser) pulses and voltage pulses are applied together to the tissue being examined. This permits first a Mode 1 examination, and then a Mode 2 and Mode 3 examination to be performed.

Thus a Mode 1 examination, involving merely measuring the impedance of the tissue, can be performed by the application only of the voltage pulses from voltage source 30 (FIG. 3), since such an impedance measurement has an excellent ability of distinguishing between fat, muscle, bone and other human tissues and to define tumor margins in an accuracy scale of about 200 cells. Such an impedance measuring mode may be that described in the above-cited patent application Ser. No. 10/035,428. As described therein, the voltage pulse source sends a pulse via transmission line 28 to the probe 20 which applies the voltage pulses to the examined tissue, detects the impedance of the examined tissue, and utilizes the detected changes in impedance for determining the extent target cells are present in the examined tissue, thereby distinguishing the type of tissue examined.

As more particularly described in that patent application, the probe generates an electrical fringe field in the examined tissue and produces reflected pulses therefrom. The reflected electrical pulses are detected and compared with respect to the applied electrical pulses to provide an indication of the dielectric properties of the examined tissue, and thereby of the type of tissue then contacted by the probe. The voltage pulses are measured by a high-speed digitizer, and are then transformed to the frequency domain mathematically. Since the present invention preferably includes, but does not require, the specific biological tissue impedance measuring technique in that patent application, further details of that biological tissue impedance measuring system and method are not set forth herein.

When the probe 20 is determined to be within the area of the tumor site, the apparatus is switched-over to a Mode 2 and 3 operation in order to more accurately determined the extent of the target cells present in the examined tissue. During this Mode 3 operation, the laser source 40 is actuated to produce a train of laser pulses which are applied to the examined tissue via the optical fiber 24 within probe 20 concurrently with the application of the voltage pulses applied by voltage pulse source 30 to the examined tissue via the coaxial conductors 21, 22 of the probe 20. In this mode, the laser source 40 produces a train of nanosecond pulses of small viz-nir (visible-near infra-red) light via optical chopper 41 which modulates the frequency of the optical pulses in order to produce a more precise indication of the extent target cells are present in the examined tissue.

Thus during the Mode 3 operation, the electrical impedance measurement is set to detect impedance changes that are at the same frequency as the optical pulse train modulation frequency of chopper 41. For example: if the repetition rate of the electrical pulses is 500 KHz and the repetition of the laser pulse is 2 KHz with modulation of 500 Hz, the impedance measurement is set to detect changes in the 500 Hz band. In this mode, the digitizing process is as in Mode 1, e.g., as described in the above-cited patent application Ser. No. 10/035,428, but the system no longer compares pair of electrical voltage pulses (incident and reflected). Instead it looks for the changes in reflected pulse amplitude only at the modulation frequency as described above in the description of the lock-in method.

This feature produces a new important advantage: If the probe does not point on cancerous cells, no electrical impedance changes will be detected; but if the probe points on cancerous cells containing the attached nano/micro-particles of light-sensitive material, a substantial change of impedance is induced. Since the detection method looks for changes at the modulation frequency, its sensitivity increases dramatically such that even one cancerous cell will induce a total change in the detected impedance.

Thus, as described above, the lock-in method utilizing the lock-in amplifier in the impedance measuring sub-system 60 of FIG. 3 utilizes the signal generated by the impedance changes at the examined tissue by a sinus function at the modulation frequency and integrates this signal over a time interval. This known lock-in measurement technique reduces the noise many orders of magnitude since the noise is not modulated and therefore its integral is summed towards zero.

The change of reflected amplitude at each measurement point is saved in the memory (e.g., 15, FIG. 1) and is sent to the analysis program.

The analysis program during the Mode 1 operation (i.e., wherein only voltage pulses are applied to the examined tissue), is the same as described in the above-cited patent application Ser. No. 10/035,428. As indicated earlier, the Mode 1 operation is capable of detecting changes in impedance of the examined tissue sufficiently for determining the type of tissue sufficient to locate the tumor and to remove it. However, in order to determine whether tissue adjacent to the removed tissue may also be cancerous and should therefore be removed, a Mode 2 and Mode 3 examination is performed to detect changes in the electrical characteristics and in the optical characteristics of the examined tissue, and to utilize such detected characteristics for more accurately determining the presence of cancerous cells in the examined tissue.

In Modes 2 and 3, the analysis program looks for different features in order to detect cancerous cells.

Thus, the analysis checks the data array and looks for local, same point, changes of impedance during the light activation. If a change exists, it is due the existence of the physical element nano/micro-particles, and therefore confirms cancer cell presence in the tissue under the tip of the probe. The surgeon thus receives a clear indication of cancerous cell, e.g., by an audio output from the user interface unit 90.

The analysis also compares the light reflection from each tissue point with respect to that from the previous tissue point. It is also looks for a distinct features of light reflection due the existence of the physical elements attached to the cancerous cells; absorption at certain frequency, emission at certain frequency (florescence), a change of polarization as a function of frequency, and total change at reflection (average) of the reflection over the full spectrum. When the analysis finds a parameter that is a unique for the physical element in the contrast agent, this provides a clear indication of a cancerous cell.

The measurement of changes in impedance during the Mode 3 examination is performed by the impedance-measuring sub-system 60 of FIG. 3. As described above, sub-system 60 includes a digitizing unit and a lock-in amplifier for producing a measurement which is characterized by a high signal-to-noise ratio.

The measurement of changes in the optical characteristics of the examined tissue, according to the Mode 2 examination, is performed by the optical analyzer sub-system 70 in FIG. 3, including the optical splitting box 80, its polarizing cube 82, and the two spectrometers 71 and 72.

As briefly described above, and as more particularly illustrated in FIG. 8, the modulated laser beam from the optical chopper 41 is split by beam splitter 81 in the splitting box 80 into a main beam which carries most of the optical energy to the tissue being examined, and a secondary beam to the two spectrometers 71, 72, via the polarizing cube 82 which produces two polarizations of the beams. This is done in order to measure the pulse spectrum of the incident optical beam and of the reflected optical beam at each polarization separately. Such information enables an analysis to be made of the changes in the optical characteristics of the examined tissue produced by the nano/micro-particles therein, which changes in optical characteristics may be utilized particularly with the changes in the electrical properties characteristics measured by sub-system 60, to provide a relatively accurate determination of whether any cancerous cells are present in the examined tissue.

FIGS. 9a and 9b show how the polarization function is calculated from the readings of the two spectrometers 71, 72. Each spectrometer digitizes the power amplitude of light at each frequency. The light directed to each of the spectrometers is of a different polarity. Accordingly, at certain frequencies the relation between the amplitudes of the two spectrometers gives the polarity. The relation calculation is repeated at all measured frequencies, and the polarization function is measured. This is done for the incident pulse. For the reflected pulse, the change in polarities is again calculated and recorded.

Since the apparatus, when operated as described above, has detected cancerous cells with a relatively high accuracy, the apparatus may now be operated according to a fourth mode (Mode 4) for destroying the detected cells by ablation without the need for aiming it again since it is already in the place. This may be done automatically when detecting cancerous cells, or on demand, by activating the laser to transmit high-power short duration pulses at the detected spot of the examined tissue. The ablation pulses should be of femtosecond pulse duration with energy per pulse of about 100 nj up to about 1 mj.

Modifications in the Probe Structure

Figure 11:
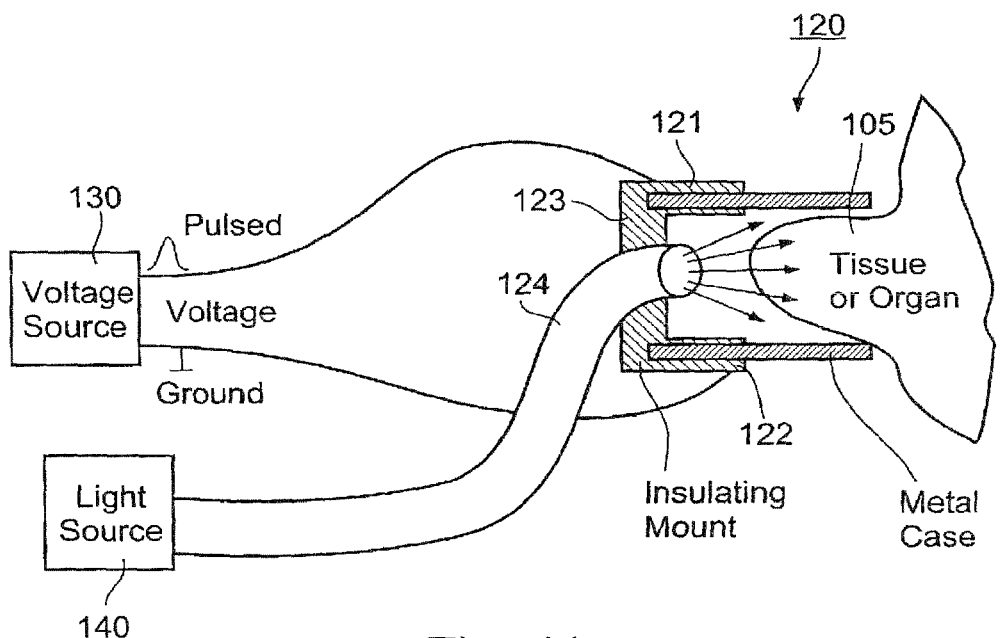
FIGS. 11 and 12 illustrate possible variations in the construction of the electrical probe.

FIG. 11 schematically illustrates a possible modification in the construction of the electro-optic probe, therein generally designated 120, for use in examining tissue 105. Probe 120 includes two capacitor plates 121, 122, mounted on a dielectric mounting 123 and connected to a voltage source 130 for applying the voltage pulses to the examined tissue. Probe 120 further includes an optical fiber 124 received within an opening of the dielectric mounting plate 123 between the two capacitor plates 121, 122, and connected to a light source 140, such as a laser, for applying the optical pulses to the examined tissue. Probe 120 may be used in apparatus constructed and operating as described above.

Figure 12:
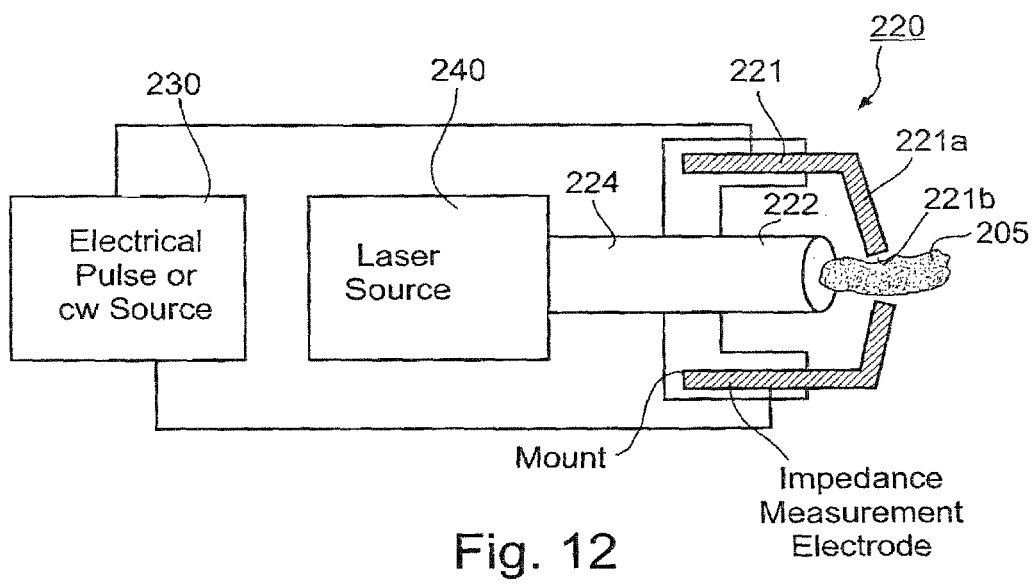

FIG. 12 illustrates another variation wherein the probe, therein generally designated 220, includes an outer conductor 221 and an inner conductor 222 in the form of a metal coating on an optical fiber 223. The outer conductor 221 is closed by an end wall 221a at the operative end of the probe, which end wall is formed with an opening 221b for receiving the tissue 205 to be examined.

Probe 220 illustrated in FIG. 12 is otherwise the same as described above, including an electrical pulse source 230 connected to the two conductors 221, 222 for applying voltage pulses to the tissue, and a laser source 240 for applying optical pulses via optical fiber 223 to the tissue.

Figure 13A:
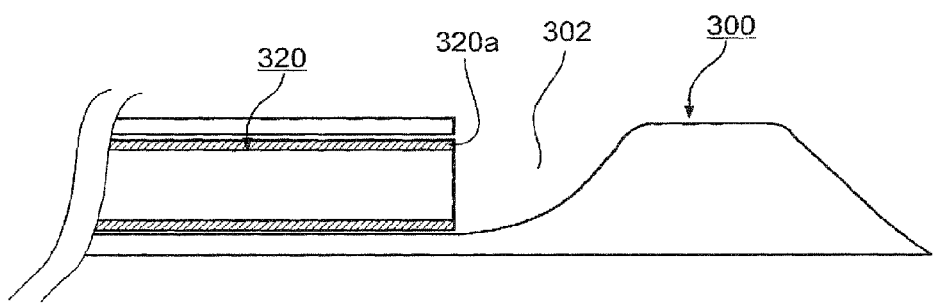
FIG. 13a schematically illustrates a possible variation in the probe construction that enables the use of the probe inside a biopsy/needle/tool.

FIG. 13a illustrates the probe, therein generally designated 320, incorporated in a biopsy needle 300 having a needle cavity 302. Such a biopsy needle may be about 2 mm in diameter. As shown in FIG. 13a, the probe 320 is located within the needle with the operative end 320a of the probe facing the cavity 302 for examining the biopsy specimen obtained by the needle.

Figure 13B:
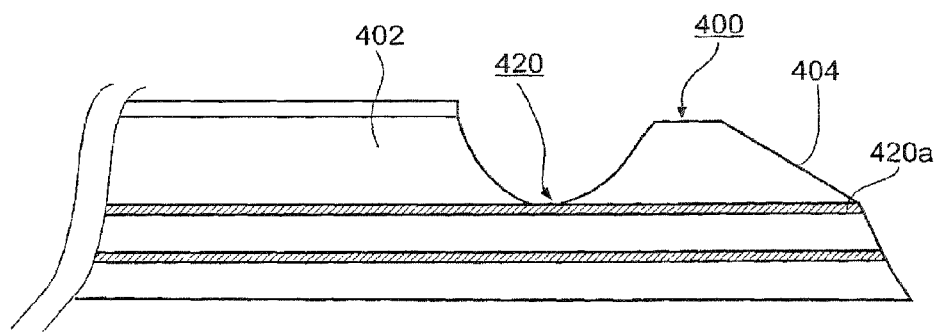
FIG. 13b schematically illustrates a possible variation in the probe construction that enables the use of the probe in front of the biopsy/needle/tool.

FIG. 13b illustrates a biopsy needle 400 including a side cavity 402 and a front sharp edge 404. As shown in FIG. 13b, the probe 420 is located within the biopsy needle such that the operative 420a of the probe is in front of the sharp front edge 404.

Probe 20 illustrated in FIG. 10 is constructed so as to be manually graspable and manipulatable with respect to the tissue to be examined. Such a probe, however, can be constructed so as to be of a size and of sufficient flexibility to enable it to be introduced into the body of a subject via a catheter for examining selected tissue in accordance with the above-described Modes 1, 2 or 3, and/or for ablating selected tissue in order to destroy detected cancerous cells as described above with respect to Mode 4.

Figure 14:
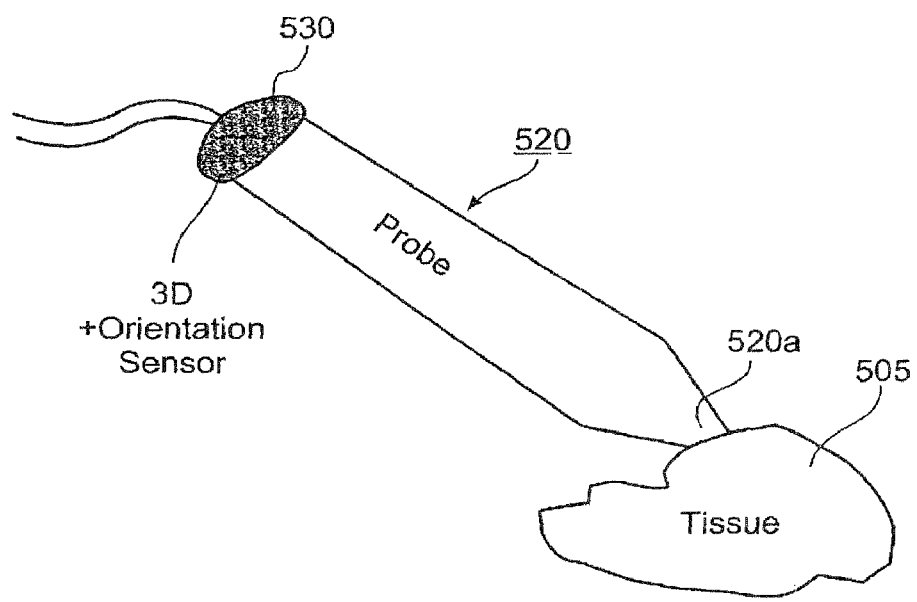
FIG. 14 illustrates another probe constructed to include a 3-D orientation sensor to enable determination of the position and orientation of the operative end of the probe.
Figure 14A:
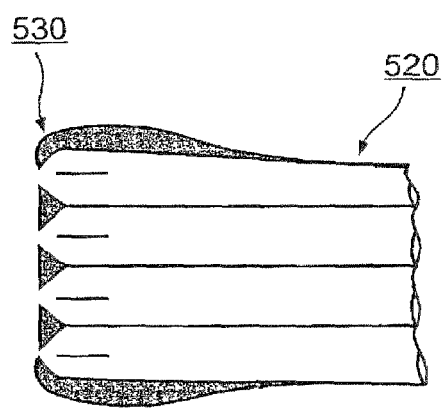
FIG. 14a is a fragmentary view illustrating the orientation sensor in the probe of FIG. 14.
Figure 14B:
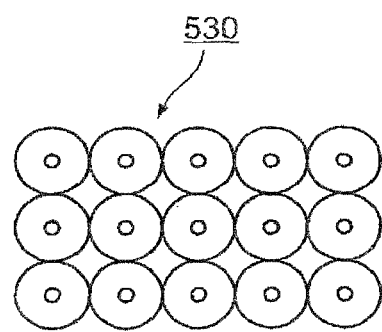
FIG. 14b is a plan view schematically illustrating the orientation sensor in the probe of FIG. 14.

In addition, the probe could equipped with a 3-D coordinate orientation sensor for determining the location and orientation of the operative end of the probe, and thereby of the tissue being examined. FIG. 14 illustrates such a probe, therein generally designated 500, including an orientation sensor in the form of a rectangular array or matrix of optical sensor elements 520 at the back end of the probe and at a known location with respect to the operative end 500a of the probe. FIG. 14a more particularly illustrates the back end of the probe 520 carrying the matrix of optical sensor elements 530, and FIG. 14b schematically illustrates the matrix of the optical sensor elements. It will be appreciated that any 3-D orientation sensor construction and measuring system could be used with this application of the invention.

It will also be appreciated that the sensor array 530 could all be used for imagining the examined tissue 505 and for displaying its image in a real-time manner during the course of the surgical operation.

Another variation would be to provide the probe with a thimbal-type mounting device for mounting it on the surgeon's fingertip. Further, while the embodiments described above included only one pair of electrodes for applying voltage pulses, the probe could include a plurality of such pairs, e.g., in the form of micro-electrodes, at the operative end of the probe.

While the invention has been described with respect to several preferred embodiments, it will be appreciated that these are set forth merely for purposes of example, and that many variations may be made. For example, the apparatus could be used for targeting other cells, such as bacteria, etc., which are selectively bindable to an antibody conjugated with the nano/micro-particles. In addition, the apparatus and method could be used for examining, cells off-line, e.g., in examining pre-operation biopsies or post-operation samples of removed tissue. Further, while the above selective-bonding technique is described above with respect to using antibodies, it will be appreciated that other biological carriers could be used for this purpose instead of antibodies. Other electrical-characteristic measuring techniques and/or light-measuring techniques may be used. Many other variations and applications of the invention will be apparent.

What is claimed is:

1. A method for examining a tissue region containing target cells, wherein the tissue region is an excised tissue region and has an exposed surface, the method comprising:
    applying a probe device to the excised tissue region, said applying comprising bringing an operative end of the probe into contact with said exposed surface and moving said operative end over the exposed surface; and
    examining the exposed surface of said excised tissue region using said probe, determining an extent of target cells in said tissue region, thereby defining margins for the target cells within said tissue region, and providing output data corresponding to results of the examination of the tissue region, thereby enabling removal of additional tissues at locations corresponding to where said margins within the tissue region include said target cells.

2. The method according to claim 1, wherein the output data includes at least one of visual and audio data.

3. The method according to claim 1, comprising analyzing the output data corresponding to the results of the examination of the tissue region indicative of the defined margins for the target cells, and removing the additional tissues.

4. The method according to claim 3, comprising examining said additional tissues.

5. The method according to claim 4, comprising removing more additional tissues until detecting that there are no target cells in the margins within the tissue region.

6. The method according to claim 1, wherein said margins of the target cells are used to provide delimitation of a healthy tissue and a tissue including said target cells.

7. The method according to claim 1, comprising examining said tissue region within a probe area defined by said probe.

8. The method according to claim 7, comprising displacing the probe area over said tissue region.

9. The method according to claim 1, wherein the target cells are cancerous cells.

10. The method according to claim 1, wherein the target cells are tumor cells.

11. The method according to claim 10, wherein the tumor cells are breast tumor cells.

12. The method according to claim 1, wherein said defining of the margins of the target cells in carried out in real-time.

13. The method according to claim 1, wherein said defining of the margins of the target cells is carried out during a surgical operation aimed at removing the target cells.

14. The method according to claim 1, comprising defining the margins of the target cells within said tissue region in an accuracy scale of at least 200 cells.

15. The method according to claim 1, comprising detecting the target cells during a surgical operation aimed at removing a tumor.

16. The method of claim 1, comprising excising the tissue region prior to said applying and examining.

17. A method of examining an excised tissue region for presence of target cells therein, comprising:
providing a probe having an operative end for applying pulses to a tissue;
contacting an exposed surface of the excised tissue region by said operative end of the probe and operating the probe while moving the operative end of the probe over the exposed surface of the excised tissue region, said operating of the probe comprising applying the pulses to examined tissue within a probe area of the exposed surface;
detecting changes in response of the tissue to said applied pulses within said probe area thereby identifying the target cells;
determining extent of presence of the target cells within said examined tissue thereby defining margins for the target cells within said exposed surface and providing output data indicative thereof;
removing additional tissues at locations adjacent to said surface and corresponding to where said margins within the examined tissue include said target cells;
examining said additional removed tissues; and
removing more additional tissues until there are no target cells in the margins within the examined tissue.

18. The method according to claim 17, wherein said pulses are energy pulses.

19. The method according to claim 17, wherein said detection in response to said applied pulses comprises detecting changes in electrical properties of said examined tissue produced by said applied energy pulses.

20. The method according to claim 17, wherein said detection in response to said applied pulses comprises detecting changes in electrical properties of said examined tissue produced by said applied energy pulses.

21. The method according to claim 17, comprising subjecting the tissue to be examined to a contrast agent containing small particles of a physical element conjugated with a biological carrier selectively bindable to said target cells.

22. The method according to claim 21, wherein said applied pulses include voltage pulses and optical pulses, and said physical element is one which changes in impedance when illuminated by an optical pulse.

23. The method according to claim 21, wherein said physical element is a light-sensitive semiconductor having an impedance which substantially decreases in the presence of light.

24. The method according to claim 21, comprising detecting changes in optical properties of said examined tissue produced by said applied optical pulses and utilizing the detected changes for determining the presence of said target cells in the examined tissue.

25. The method according to claim 17, wherein said applied energy pulses include voltage pulses, and said physical element is of a dielectric material.

26. The method according to claim 17, wherein said applied energy pulses include voltage pulses applied to the probe area of the examined tissue to detect the presence of said target cells in said probe area; and wherein optical pulses are applied to a central region of the probe area of the examined tissue to detect the extent said target cells are in said central region.

27. The method according to claim 17, wherein said probe comprises an array of optical sensors at a known location with respect to said operative end, the array of sensors being configured and operable for sensing a location and orientation of said operative end of the probe.

28. The method according to claim 17, comprising detecting the target cells in real-time during a surgical operation for removing a tumor.

29. The method according to claim 17, wherein the probe comprises a 3-D coordinate orientation sensor for determining a location and orientation of the probe.

30. The method according to claim 17, wherein the probe comprises a 3-D coordinate orientation sensor for determining a location and orientation of the examined tissue.

31. The method according to claim 30, wherein the 3-D coordinate orientation sensor is in a form of a rectangular array or matrix.

32. The method according to claim 17, wherein said pulses are laser pulses.

33. The method according to claim 32, comprising:
detecting reflections of said laser pulses from said examined tissue;
comparing an optical characteristic of the laser pulses applied to the examined tissue with that of the laser reflections from the examined tissue; and
utilizing the comparison results for determining the presence of said target cells in said examined tissue.

34. The method according to claim 33, wherein the applied and reflected laser pulses are converted into two polarization forms, and the optical characteristics of the two polarization forms are detected and compared.

35. The method according to claim 17, wherein voltage pulses are also applied to said examined tissue, and changes in impedance in said examined tissue are also detected and utilized to determine the presence of said target cells in said examined tissue.

36. The method according to claim 35, wherein said voltage pulses are applied to the probe area of the examined tissue to detect the presence of said cells in said probe area; and wherein said optical pulses are applied to a central region of the probe area of the examined tissue to detect the extent said target cells are present in said central region.

37. The method according to claim 32, wherein said laser pulses are applied at a predetermined rate; and said changes in impedance are detected at said predetermined rate to increase the signal-to-noise ratio of said detected changes in impedance.

38. A method for examining a tissue region containing target cells, the method comprising:
bringing an operative end of a probe device in contact with an exposed surface of an excised tissue region and moving the operative end over the exposed surface;
operating the probe, while moving said operative end of the probe over the exposed surface, for examining said surface of the tissue region, for determining extent of presence of target cells at said surface of the tissue region, thereby defining margins for the target cells within said surface of the tissue region, and providing output data indicative thereof,
analyzing said output data and deciding whether further removal of additional tissues is needed at locations adjacent to said surface and corresponding to where said margins within the tissue region include said target cells, enabling further examination of removed tissue samples.

39. The method according to claim 38, wherein said determining of the extent of the presence of the target cells within the tissue region comprises detected changes in characteristics of the tissue region as a result of having been subjected to a contrast agent containing small particles of a physical element conjugated with an antibody selectively bindable to the target cells.

* * * * *